(12) United States Patent
Hess et al.

(10) Patent No.: US 8,053,585 B2
(45) Date of Patent: Nov. 8, 2011

(54) PROTECTING GROUP FOR CARBOXYLIC ACIDS THAT CAN BE PHOTOLYZED BY VISIBLE LIGHT

(75) Inventors: George P. Hess, Ithaca, NY (US); Barry K. Carpenter, Slaterville Springs, NY (US); Vishakha R. Shembekar, Ithaca, NY (US); Yongli Chen, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 664 days.

(21) Appl. No.: 11/402,715

(22) Filed: Apr. 12, 2006

(65) Prior Publication Data
US 2007/0243519 A1  Oct. 18, 2007

(51) Int. Cl.
C07D 311/02 (2006.01)
C07C 229/00 (2006.01)
C07C 261/00 (2006.01)
(52) U.S. Cl. ........................ 549/283; 560/155; 560/115
(58) Field of Classification Search .................. None
See application file for complete search history.

(56) References Cited

U.S. PATENT DOCUMENTS

| | | | | |
|---|---|---|---|---|
| 5,342,970 | A | * | 8/1994 | Chalom et al. ............... 549/288 |
| 5,430,175 | A | | 7/1995 | Hess et al. |
| 5,587,509 | A | | 12/1996 | Hess et al. |
| 2002/0016472 | A1 | * | 2/2002 | Tsien et al. .................... 548/159 |

OTHER PUBLICATIONS

Abstract, Shembekar et al., Polymer Preprints (American Chemical Society, Division of Polymer Chemistry) (2004), 45(1), 893-894.*
Abstract, Epand et al., Biochimica et Biophysica Acta, Biomembranes (1996), 1284(2), 191-195.*
Ito et al., Chemical & Pharmaceutical Bulletin (1983), 31(9), 3014-23.*
CAS online citation of EP 516532, DN: 119:28004 [retrieved Sep. 10, 2008] from STN, Columbus, OH, USA.*
Suzuki et al., Organic Letters (2003), 5(25), 4867-4870.*
Database Caplus Chemical Abstracts Service, Columbus, Ohio, US; Database Accession No. 1991:679757, Abstract of Kirpichenok et al.: "Reactions of 3-iodo-7-(dialkylamino)coumarins with secondary amines." Khimiya Geterotsiklicheskikh Soedinenii (1991), (5), 609-18.*
Shembekar et al., Biochemistry 2005, 44, 7107-7114.*
Adams, "Acetylcholine Receptor Kinetics," *J. Membr. Biol.* 58:161-74 (1981).
Adams & Tsien, "Controlling Cell Chemistry with Caged Compounds," *Ann. Rev. Physiol.* 55:755-84 (1993).
Amery & Corbett, "The Synthesis and Identification of Some N-Methylated Aminonitrophenols," *J. Chem. Soc.* C 1053-7 (1967).

(Continued)

*Primary Examiner* — Karl J Puttlitz
(74) *Attorney, Agent, or Firm* — LeClairRyan

(57) ABSTRACT

The present invention relates to a photolabile compound including a coumarin family caging group covalently bound to an organic moiety containing a carboxyl group, an amino group, a sulfhydryl group, and/or a hydroxyl group. The photolabile compound, upon absorbing visible light, releases the organic moiety. Also disclosed is a method of making a photolabile compound that releases a biologically active compound upon absorbing visible light by providing an organic moiety and binding a coumarin family caging group to the organic moiety under conditions effective to make the photolabile compound. The present invention also relates to a method of obtaining a biologically active compound in a sample. The method involves adding to a sample a photolabile compound including a coumarin family caging group covalently bound to an organic moiety. The sample is then illuminated with visible light under conditions effective to obtain a biologically active compound including the organic moiety.

14 Claims, 11 Drawing Sheets

OTHER PUBLICATIONS

Amit et al., "Photosensitive Protecting Groups of Amino Sugars and Their Use in Glycoside Synthesis. 2-Nitrobenzyloxycarbonylamino and 6-Nitroveratryloxycarbonylamino Derivatives," *J. Org. Chem.* 39(2):192-6 (1974).

Amit et al., "Photosensitive Protecting Groups—A Review," *Isr. J. Chem.* 12(1-2):103-13 (1974).

Barltrop et al., "Photosensitive Protective Groups," *Chem. Commun.* 822-3 (1966).

Bartels et al., "Photochromic Activators of the Acetylcholine Receptor," *Proc. Nat'l Acad. Sci. USA* 68(8):1820-3 (1971).

Bernardinelli et al., "Flash Photolysis Using a Light Emitting Diode: An Efficient, Compact, and Affordable Solution," *Cell Calcium* 37:565-72 (2005).

Billington et al., "Synthesis and Photochemistry of Photolabile N-Glycine Derivatives and Effects of One on the Glycine Receptor," *Biochemistry* 31:5500-7 (1992).

Breitinger et al., "Synthesis and Characterization of Photolabile Derivatives of Serotonin for Chemical Kinetic Investigations of the Serotonin 5-$HT_3$ Receptor," *Biochemistry* 39:5500-8 (2000).

Breitinger, "Fast Kinetic Analysis of Ligand-Gated Ion Channels," *Neuroscientist* 7(2):95-103 (2001).

Callaway & Katz, "Photostimulation Using Caged Glutamate Reveals Functional Circuitry in Living Brain Slices," *Proc. Nat'l Acad. Sci. USA* 90:7661-5 (1993).

Chen & Okayama, "High-efficiency Transformation of Mammalian Cells by Plasmid DNA," *Mol. Cell. Biol.* 7(8):2745-52 (1987).

Cheng et al., "Photolysis of γ-(α-Carboxy-2-nitrobenzyl)-L-glutamic Acid Investigated in the Microsecond Time Scale by Time-resolved FTIR," *J. Am. Chem. Soc.* 124:7676-7 (2002).

Corrie & Trentham, "Caged Nucleotides and Neurotransmitters," in 2 Bioorganic Photochemistry: Biological Applications of Photochemical Switches 243-305 (Harry Morrison ed., 1993).

Dalva & Katz, "Rearrangements of Synaptic Connections in Visual Cortex Revealed by Laser Photostimulation," *Science* 265:255-8 (1994).

De Mayo, "Ultraviolet Photochemistry of Simple Unsaturated Systems," *Adv. Org. Chem.* 2:367-425 (1960).

Delcour & Hess, "Chemical Kinetic Measurements of the Effect of *trans*- and *cis*-3,3'-Bis[(trimethylammonio)methyl]azobenzene Bromide on Acetylcholine Receptor Mediated Ion Translocation in *Electrophorus electricus* and *Torpedo californica*," *Biochemistry* 25:1793-8 (1986).

Denk et al., "Anatomical and Functional Imaging of Neurons Using 2-Photon Laser Scanning Microscopy," *J. Neurosci. Meth.* 54:151-62 (1994).

Denk, "Two-photon Scanning Photochemical Microscopy: Mapping Ligand-gated Ion Channel Distributions," *Proc. Nat'l Acad. Sci. USA* 91:6629-33 (1994).

Dodt et al., "Circuitry of Rat Barrel Cortex Investigated by Infrared-guided Laser Stimulation," *Neuroreport* 14(4):623-7 (2003).

Dynamic Studies in Biology (Maurice Goeldner & Richard Givens eds., 2005). (Table of Contents).

Manfred Eigen, Immeasurably Fast Reactions, Nobel Lecture (Dec. 11, 1967) in Nobel Lectures: Chemistry 1963-1970, at 170-203 (1972).

Eigen, "Kinetics of Reaction Control and Information Transfer in Enzymes and Nucleic Acids," in Nobel Symposium 5: Fast Reactions and Primary Processes in Chemical Kinetics 333-69 (Stig Claesson ed., 1967).

Engert et al., "A Low-cost UV Laser for Flash Photolysis of Caged Compounds," *J. Neurosci. Meth.* 66:47-54 (1996).

Gee et al., "Caged Bioactive Carboxylates. Synthesis, Photolysis Studies, and Biological Characterization of a New Caged N-Methyl-D-aspartic Acid," *J. Org. Chem.* 60:4260-3 (1995).

Gee et al., "Desyl Esters of Amino Acid Neurotransmitters. Phototriggers for Biologically Active Neurotransmitters," *J. Org. Chem.* 61:1228-33 (1996).

Gee et al., "Synthesis and Photochemistry of a New Photolabile Derivative of GABA. Neurotransmitter Release and Receptor Activation in the Microsecond Time Region," *J. Am. Chem. Soc.* 116:8366-7 (1994).

Grewer et al., "A New Photolabile Precursor of Glycine with Improved Properties: A Tool for Chemical Kinetic Investigations of the Glycine Receptor," *Biochemistry* 39:2063-70 (2000).

Grewer et al., "Substrate Translocation Kinetics of Excitatory Amino Acid Carrier 1 Probed with Laser-pulse Photolysis of a New Photolabile Precursor of D-Aspartic Acid," *Biochemistry* 40:232-40 (2001).

Grewer, "Investigation of the $α_1$-Glycine Receptor Channel-opening Kinetics in the Submillisecond Time Domain," *Biophys. J.* 77:727-38 (1999).

Gurney & Lester, "Light-flash Physiology with Synthetic Photosensitive Compounds," *Physiol. Rev.* 67(2):583-617 (1987).

Hardie, "Photolysis of Caged $Ca^{2+}$ Facilitates and Inactivates but Does Not Directly Excite Light-sensitive Channels in *Drosophila* Photoreceptors," *J. Neurosci.* 15(1):889-902 (1995).

Hartridge & Roughton, "A Method of Measuring the Velocity of Very Rapid Chemical Reactions," *Proc. Roy. Soc. London A* 104:376-94 (1923).

Hess, "Determination of the Chemical Mechanism of Neurotransmitter Receptor-mediated Reactions by Rapid Chemical Kinetic Techniques," *Biochemistry* 32(4):989-1000 (1993).

Hess, "Rapid Chemical Reaction Techniques Developed for Use in Investigations of Membrane-bound Proteins (Neurotransmitter Receptors)," *Biophys Chem.* 100:493-506 (2003).

Jayaraman et al., "Fourier Transform Infrared Spectroscopic Characterization of a Photolabile Precursor of Glutamate," *FEBS Lett.* 475:278-82 (2000).

Jayaraman et al., "How Fast Does the γ-Aminobutyric Acid Receptor Channel Open? Kinetic Investigations in the Microsecond Time Region Using a Laser-pulse Photolysis Technique," *Biochemistry* 38:11372-8 (1999).

Jayaraman, "Channel-opening Mechanism of a Kainate-activated Glutamate Receptor: Kinetic Investigations Using a Laser-pulse Photolysis Technique," *Biochemistry* 37:16735-40 (1998).

Jayaraman et al., "Ligand-Protein Interactions in the Glutamate Receptor," *Biochemistry* 39(30):8693-7 (2000).

Kandler et al., "Focal Photolysis of Caged Glutamate Produces Long-term Depression of Hippocampal Glutamate Receptors," *Nat. Neurosci.* 1(2):119-23 (1998).

Kaplan et al., "Rapid Photolytic Release of Adenosine 5'-Triphosphate from a Protected Analogue: Utilization by the Na:K Pump of Human Red Blood Cell Ghosts," *Biochemistry* 17(10):1929-35 (1978).

Katz & Dalva, "Scanning Laser Photostimulation. A New Approach for Analyzing Brain Circuits," *J. Neurosci. Meth.* 54:205-18 (1994).

Knowles, "Photogenerated Reagents for Biological Receptor-site Labeling," *Acc. Chem. Res.* 5:155-60 (1972).

Kuzmič et al., "Photochemical Hydrolysis of Some Nitrophenyl Acetates," *Collec. Czech. Chem. Commun.* 51:1293-1300 (1986).

Lester & Nerbonne, "Physiological and Pharmacological Manipulations with Light Flashes," *Ann. Rev. Biophys. Bioeng.* 11:151-75 (1982).

Li & Niu, "How Fast Does the GluR1$Q_{flip}$ Channel Open?," *J. Biol. Chem.* 279(6):3990-7 (2004).

Li et al., "Channel-opening Kinetics of GluR2$Q_{flip}$ AMPA Receptor: A Laser-Pulse Photolysis Study," *Biochemistry* 42:12358-66 (2003).

Li et al., "Channel-opening Kinetics of GluR6 Kainate Receptor," *Biochemistry* 42:12367-75 (2003).

Li et al., "Kinetic Mechanism of Channel Opening of the GluRD$_{flip}$ AMPA Receptor," *Biochemistry* 44:5835-41 (2005).

Madden et al., "Stereochemistry of Quinoxaline Antagonist Binding to a Glutamate Receptor Investigated by Fourier Transform Infrared Spectroscopy," *J. Biol. Chem.* 276(41):37821-6 (2001).

Mascia et al., "Enhancement of Homomeric Glycine Receptor Function by Long-chain Alcohols and Anaesthetics," *Br. J. Pharmacol.* 119:1331-6 (1996).

Matsubara et al., "How Fast Does an Acetylcholine Receptor Channel Open? Laser-pulse Photolysis of an Inactive Precursor of Carbamoylcholine in the Microsecond Time Region with $BC_3H1$ Cells," *Biochemistry* 31:5507-14 (1992).

Matsuzaki et al., "Dendritic Spine Geometry Is Critical for AMPA Receptor Expression in Hippocampal CA1 Pyramidal Neurons," *Nature Neurosci.* 4(11):1086-92 (2001).

McCray & Trentham, "Properties and Uses of Photoreactive Caged Compounds," *Ann. Rev. Biophys. Biophys. Chem.* 18:239-70 (1989).

McCray et al., "A New Approach to Time-resolved Studies of ATP-requiring Biological Systems: Laser Flash Photolysis of Caged ATP," *Proc. Nat'l Acad. Sci. USA* 77(12):7237-41 (1980).

291 Methods in Enzymology: Caged Compounds 1-529 (Gerard Mariott ed., 1998) (Table of Contents).

Milburn et al., "Synthesis, Photochemistry, and Biological Activity of a Caged Photolabile Acetylcholine Receptor Ligand," *Biochemistry* 28:49-55 (1989).

Morrison, "The Photochemistry of the Nitro and Nitroso Groups," *in* 1 The Chemistry of the Nitro and Nitroso Groups 165-213 (Henry Feuer ed., 1st ed. 1969).

Muralidharan & Nerbonne, "Photolabile 'Caged' Adrenergic Receptor Agonists and Related Model Compounds," *J. Photochem. Photobiol (B)* 27:123-37 (1995).

Muralidharan et al., "'Caged' Phenylephrine: Development and Application to Probe the Mechanism of α-Receptor Mediated Vasoconstriction," *Proc. Nat'l Acad. Sci. USA* 90:5199-203 (1993).

Steven L. Murov et al., Handbook of Photochemistry 298-313 (2d. ed. 1993).

Nerbonne, "Caged Compounds: Tools for Illuminating Neuronal Responses and Connections," *Curr. Opin. Neurobiol.* 6:379-86 (1996).

Niu & Hess, "An Acetylcholine Receptor Regulatory Site in $BC_3H1$ Cells: Characterized by Laser-pulse Photolysis in the Microsecond-to-millisecond Time Region," *Biochemistry* 32(15):3831-5 (1993).

Niu et al., "Chemical Kinetic Investigations of Neurotransmitter Receptors on a Cell Surface in the µs Time Region," *in* VII Techniques in Protein Chemistry 139-49 (Daniel R. Marshak ed., 1996).

Niu et al., "Cocaine: Mechanism of Inhibition of a Muscle Acetylcholine Receptor Studied by Laser-pulse Photolysis Technique," *Proc. Nat'l Acad. Sci. USA* 92:12008-12 (1995).

Niu et al., "Synthesis and Characterization of a Caged Receptor Ligand Suitable for Chemical Kinetic Investigations of the Glycine Receptor in the 3-µs Time Domain," *Biochemistry* 35:8136-42 (1996).

Niu et al., "Synthesis and Photochemical Properties of a Kainate Precursor and Activation of Kainate and AMPA Receptor Channels on a Microsecond Time Scale," *Biochemistry* 35:2030-6 (1996).

Papageorgiou & Corrie, "Synthesis and Properties of Carbamoyl Derivatives of Photolabile Benzoins," *Tetrahedron* 53(11):3917-32 (1997).

Parpura & Haydon, "UV Photolysis Using a Micromanipulated Optical Fiber to Deliver UV Energy Directly to the Sample," *J. Neurosci. Meth.* 87:25-34 (1999).

Patchornik et al., "Photosensitive Protecting Groups," *J. Am. Chem. Soc.* 92(21):6333-5 (1970).

Pei et al., "GluR3 Flip and Flop: Differences in Channel Opening Kinetics," *Biochemistry* 46:2027-36 (2007).

Pelliccioli & Wirz, "Photoremovable Protecting Groups: Reaction Mechanisms and Applications," *Photochem. Photobiol. Sci.* 1:441-58 (2002).

Ramakrishnan & Hess, "On the Mechanism of a Mutated and Abnormally Functioning γ-Aminobutyric Acid (A) Receptor Linked to Epilepsy," *Biochemistry* 43:7534-40 (2004).

Ramesh et al., "Photolysis of a Protecting Group for the Carboxyl Function of Neurotransmitters Within 3 µs and with Product Quantum Yield of 0.2," *Proc. Nat'l Acad. Sci. USA* 90:11074-8 (1993).

Rapp, "Flash Lamp-based Irradiation of Caged Compounds," *Meth. Enzymol.* 291:202-22 (1998).

Sheehan & Hess, "A New Method of Forming Peptide Bonds," *J. Am. Chem. Soc.* 77:1067-8 (1955).

Sheehan & Wilson, "Photolysis of Desyl Compounds. A New Photolytic Cyclization," *J. Am. Chem. Soc.* 86:5277-81 (1964).

Sheehan et al., "The Photolysis of Methoxy-substituted Benzoin Esters. A Photosensitive Protecting Group for Carboxylic Acids," *J. Am. Chem. Soc.* 93(26):7222-8 (1971).

Shembekar et al., "Development of Photolabile Protecting Groups That Rapidly Release Bioactive Compounds on Photolysis with Visible Light," *Polymer Preprints* 45(1):893-4 (2004).

Takaoka et al., "Synthesis and Photoreactivity of Caged Blockers for Glutamate Transporters," *Bioorg. Med. Chem. Lett.* 13:965-70 (2003).

Volgraf et al., "Reversibly Caged Glutamate: A Photochromic Agonist of Ionotropic Glutamate Receptors," *J. Am. Chem. Soc.* 129:260-1 (2006).

Walker et al., "Photolabile 1-(2-Nitrophenyl)ethyl Phosphate Esters of Adenine Nucleotide Analogues. Synthesis and Mechanism of Photolysis," *J. Am. Chem. Soc.* 110:7170-7 (1988).

Walker et al., "Photolabile Protecting Groups for an Acetylcholine Receptor Ligand. Synthesis and Photochemistry of a New Class of o-Nitrobenzyl Derivatives and Their Effects on Receptor Function," *Biochemistry* 25:1799-1805 (1986).

Walker et al., "Rapid Release of an α-Adrenergic Receptor Ligand from Photolabile Analogues," *Biochemistry* 32:1338-45 (1993).

Wieboldt et al., "Synthesis and Photochemistry of Photolabile Derivatives of γ-Aminobutyric Acid for Chemical Kinetic Investigations of the γ-Aminobutyric Acid Receptor in the Millisecond Time Region," *Biochemistry* 33:1526-33 (1994).

Wilcox et al., "Synthesis of Photolabile 'Precursors' of Amino Acid Neurotransmitters," *J. Org. Chem.* 55:1585-9 (1990).

Wootton & Trentham, "'Caged' Compounds to Probe the Dynamics of Cellular Processes: Synthesis and Properties of Some Novel, Photosensitive P-2-Nitrobenzyl Esters of Nucleotides," *in* 272 NATO Science Series C: Photochemical Probes in Biochemistry 277-96 (Peter E. Nielsen ed., 1989).

Xu et al., "Multiphoton Fluorescence Excitation: New Spectral Windows for Biological Nonlinear Microscopy," *Proc. Nat'l Acad. Sci. USA* 93:10763-8 (1996).

Banerjee et al., "Protecting Group Release Through Photoinduced ElectronTransfer: Wavelength Control Through Sensitized Irradiation," *Tetrahedron Lett.* 39:4635-4638 (1998).

Banerjee et al., "Toward the Development of New Photolabile Protecting Groups That Can Rapidly Release Bioactive Compounds upon Photolysis with Visible Light," *J. Org. Chem.* 68:8361-8367 (2003).

Barltrop et al., "Photosensitive Protecting Groups," *Tetrahedron Lett.* 16:697-699 (1962).

Bochet, C. G. "Orthogonal Photolysis of Protecting Groups," *Angew. Chem. Int. Ed.* 40(11):2071-2073 (2001).

Bochet, C. G. "Photolabile Protecting Groups and Linkers," *J. Chem. Soc., Perkin Trans.* 1:125-142 (2002).

Bochet, C. G., "Wavelength-Selective Cleavage of Photolabile Protecting Groups," *Tetrahedron Lett.* 41:6341-6346 (2000).

Canepari et al., "Photochemical and Pharmacological Evaluation of 7-Nitroindolinyl- and 4-Methoxy-7-Nitroindolinyl-Amino Acids as Novel, Fast Caged Neurotransmitters," *J. Neurosci. Methods* 112:29-42 (2001).

Furuta et al., "Brominated 7-hydroxycoumarin-4-ylmethyls: Photolabile Protecting Groups with Biologically Useful Cross-Sections for Two Photon Photolysis," *Proc. Natl. Acad. Sci., U.S.A.* 96:1193-1200 (1999).

Furuta et al., "Photochemical Properties of New Photolabile cAMP Derivatives in a Physiological Saline Solution," *J. Org. Chem.* 60:3953-3956 (1995).

Gee et al., "Desyl Esters of Amino Acid Neurotransmitters. Photoriggers for Biologically Active Neurotransmitters," *J. Org. Chem.* 61:1228-1233 (1996).

Gee et al., "Synthesis, Photochemistry, and Biological Characterization of Photolabile Protecting Groups for Carboxylic Acids and Neurotransmitters," *Methods in Enzymology* 291:30-50 (1998).

Geißler et al., "(Coumarin-4-yl) methyl Esters as Highly Efficient, Ultrafast Phototriggers for Protons and Their Application to Acidifying Membrane Surfaces," *Angew. Chem. Int. Ed.* 44:1195-1198 (2005).

Geißler et al., "DMACM-Caged Adenosine Nucleotides: Ultrafast Phototriggers for ATP, ADP, and AMP Activated by Long-Wavelength Irradiation," *ChemBioChem* 4:162-170 (2003).

Givens et al., "Photochemistry of Phosphate Esters: an Efficient Method for the Generation of Electrophiles," *J. Am. Chem. Soc.* 106:6860-6861 (1984).

Hagen et al., "[7-(Dialkylamino)coumarin-4-yl]methyl-caged Compounds as Ultrafast and Effective Long-Wavelength Phototriggers of 8-Bromo-Substituted Cyclic Nucleotides," *ChemBioChem* 4:434-442 (2003).

Hagen et al., "Highly Efficient and Ultrafast Phototriggers for cAMP and cGMP by Using Long-Wavelength UV/Vis-Activation," *Angew. Chem. Int. Ed.* 40(6):1045-1048 (2001).

Hagen et al., "Synthesis, Photochemistry and Application of (7-methoxycoumarin-4-yl)methyl-caged 8-bromoadenosine Cyclic 3',5'-monophosphate and 8-bromoguanosine Cyclic 3',5'-monophosphate Photolyzed in the Nanosecond Time Region," *J. Photochem. Photobiol. B* 53:91-102 (1999).

Hess, G.P., "Design and Application of Caged Neurotransmitters," in *Imaging Living Cells*, Yuste et al., Cold Spring Harbor Press, pp. 25.1-25.18 (1999).

Hess et al., "Development and Application of Caged Ligands for Neurotransmitter Receptors in Transient Kinetic and Neuronal Circuit Mapping Studies," *Methods in Enzymology* 291:443-473 (1998).

Hess, G.P., "Photochemical Release of Neurotransmitters—Transient Kinetic Investigations of Membrane-Bound Receptors on the Surface of Cells in the Microsecond-to-Millisecond Time Region," in *Dynamic Studies in Biology Phototriggers, Photswitches and Cages Biomolecules*, Gardner, M., Wiley, pp. 205-231 (2005).

Hess, G.P., "Rapid Chemical Reaction Techniques Developed for Use in Investigations of Membrane-Bound Proteins (Neurotransmitter Receptors)," *Biophys. Chem.* 100:493-506 (2003).

Kotter et al., "Analysing Functional Connectivity in Brain Slices by a Combination of Infrared Video Microscopy, Flash Photolysis of Caged Compounds and Scanning Methods," *Neuroscience* 86(1):265-277 (1998).

Li et al., "Identification of Chemical Synapses in the Pharynx of *Caenorhabditis elegans*," *Proc. Natl. Acad. Sci. U.S.A.* 94:5912-5916 (1997).

Lin et al., "A Strategy for the Construction of Caged Diols Using a Photolabile Protecting Group," *J. Org. Chem.* 67:2723-2726 (2002).

Lu et al., "Bhc-diol as a Photolabile Protecting Group for Aldehydes and Ketones," *Org. Lett.* 5(12):2119-2122 (2003).

Mizuta et al., "Design, Synthesis, Photochemical Properties and Cytotoxic Activities of Water-Soluble Caged L-Leucyl-L-Leucine Methyl Esters that Control Apoptosis of Immune Cells," *Bioorg. Med. Chem.* 10:675-683 (2002).

Park et al., "New Photoactivated Protecting Groups. 6. p-Hydroxyphenacyl: A Phototrigger for Chemical and Biochemical Probes," *J. Am. Chem. Soc.* 119, 2453-2463 (1997).

Pillai, V. N. R. "Photolytic Deprotection and Activation of Functional Groups," *Org. Photochem.* 9:225-317 (1987).

Pirrung, et al., "3'-Nitrophenylpropyloxycarbonyl (NPPOC) Protecting Groups for High-Fidelity Automated 5' → 3' Photochemical DNA Synthesis," *Organic Letters* 3(8):1105-1108 (2001).

Schönleber et al., "Rapid Photolytic Release of Cytidine 5'-Diphosphate from a Coumarin Derivative: a New Tool for the Investigation of Ribonucleotide Reductases," *Bioorg. Med. Chem.* 10:97-101 (2002).

Schupp et al., "Mechanistic Studies of the Photorearrangement of o-Nitrobenzyl Esters," *J. Photochem.* 36:85-97 (1987).

Shembekar et al., "A Protecting Group for Carboxylic Acids That Can Be Photolyzed by Visible Light," *Biochemistry* 44:7107-7114 (2005).

Singh et al., "Synthesis and Photochemical Properties of Nitro-Naphthyl Chromophore and the Corresponding Immunoglobulin Bioconjugate," *Bioconjugate Chem.* 13:1286-1291 (2002).

Suzuki et al., "Coumarin-4-ylmethoxycarbonyls as Phototriggers for Alcohols and Phenols," *Organic Letters* 5(25):4867-4870 (2003).

Takaoka et al., "Synthesis of Carbamate-Type Caged Derivatives of a Novel Glutamate Transporter Blocker," *Bioorg. Med. Chem.* 12:3687-3694 (2004).

Wieboldt et al., "Photolabile Precursors of Glutamate: Synthesis, Photochemical Properties, and Activation of Glutamate Receptors on a Microsecond Time Scale," *Proc. Natl. Acad. Sci. U.S.A.* 91:8752-8756 (1994).

Zhu et al., "Formation and Decay of Nitronic Acid in the Photorearrangement of o-Nitrobenzyl Esters," *J. Photochem.* 39:317-332 (1987).

\* cited by examiner

PROTECTING GROUP FOR CARBOXYLIC ACIDS THAT CAN BE PHOTOLYZED BY VISIBLE LIGHT

This invention arose out of research sponsored by the National Institutes of Health (Grant No. GM 04842). The U.S. Government may have certain rights in this invention.

FIELD OF THE INVENTION

The present invention relates to photolabile compounds including a coumarin family caging group covalently bound to an organic moiety, where the compound, upon absorbing visible light, releases the organic moiety. The present invention also relates to methods of making a photolabile compound that releases a biologically active compound upon absorbing visible light, as well as methods of obtaining a biologically active compound in a sample.

BACKGROUND OF THE INVENTION

The photorelease of bioactive molecules from photoprotected precursors is a powerful tool for studying fast kinetic biochemical responses in cell or tissue culture (Hess et al., "Development and Application of Caged Ligands for Neurotransmitter Receptors in Transient Kinetic and Neuronal Circuit Mapping Studies," *Methods in Enzymology* 291:443-473 (1998); Pelliccioli et al., "Photoremovable Protecting Groups: Reaction Mechanisms and Applications," *Photochem Photobiol Sci* 1:441-458 (2000); Goeldner, eds., *Dynamic Studies in Biology: Phototriggers, Photoswitches, and Caged Biomolecules*; Wiley-VCH: Weinheim, Germany (2005)). The photolabile caged forms of these bioactive molecules do not evoke biological responses when applied. Besides, in addition to temporal resolution, good spatial resolution is also achieved by the use of these precursors. In caged compounds, the biological activity of the molecule is blocked by chemical modification. A photosensitive protecting group is introduced at the functional group of the biologically active molecule that can later be removed by light of a particular wavelength. Thus, fast jumps in the concentration of the biomolecule can be achieved at a definite location.

Photolabile protecting groups for functional groups commonly found in biologically important compounds have been developed during the last 40 years (De Mayo P., "Ultraviolet Photochemistry of Simple Unsaturated Systems," *Adv Org Chem* 2:367-425 (1960); Barltrop et al., "Photosensitive Protective Groups," *J Chem Soc, Chem Commun* 822-823 (1966); Knowles J., "Photogenerated Reagents for Biological Receptor-Site Labeling," *Acc Chem Res* 5:155-160 (1972); Patchornik et al., "Photosensitive Protecting Groups," *J Am Chem Soc* 92:6333-6335 (1970)). To solve biological problems, they were first used by Kaplan et al. to rapidly generate significant and known concentrations of biologically active compounds (Kaplan et al., "Rapid Photolytic Release of Adenosine 5'-Triphosphate From a Protected Analogue: Utilization by the Na:K Pump of Human Red Blood Cell Ghosts," *Biochemistry* 17:1929-1935 (1978)). The rapid release of biologically active compounds from photolabile precursors has become a very useful technique in transient kinetic investigations of neurotransmitter receptors. These proteins must be studied on cell surfaces, where rapid mixing techniques do not have the time resolution required for the investigation of the fast (microsecond to millisecond) processes involved in activation and inhibition of neurotransmitters receptors (Udgaonkar et al., "Chemical Kinetic Measurements of a Mammalian Acetylcholine Receptor by a Fast-Reaction Technique," *Proc Natl Acad Sci USA* 84:8758-8762 (1987); Jayaraman et al., "How Fast Does the Gamma-Aminobutyric Acid Receptor Channel Open? Kinetic Investigations in the Microsecond Time Region Using a Laser-Pulse Photolysis Technique," *Biochemistry* 38:11372-11378 (1999); Grewer et al., "On the Mechanism of Inhibition of the Nicotinic Acetylcholine Receptor by the Anticonvulsant MK-801 Investigated by Laser-Pulse Photolysis in the Microsecond-to-Millisecond Time Region," *Biochemistry* 38:7837-7846 (1999); Ramakrishnan et al., "On the Mechanism of a Mutated and Abnormally Functioning γ-Aminobutyric Acid (A) Receptor Linked to Epilepsy," *Biochemistry* 43:7534-7540 (2004)). This problem is overcome by equilibrating the cell surface receptors with a biologically inactive caged neurotransmitter. The reaction to be investigated is initiated in the As time domain by photolysis of the caged compound (Hess G., "Rapid Chemical Reaction Techniques Developed for Use in Investigations of Membrane-Bound Proteins (Neurotransmitter Receptors)," *Biophys Chem* 100:493-506 (2003)). The α-carboxy-2-nitrobenzyl photolabile protecting group (Milburn et al., "Synthesis, Photochemistry, and Biological Activity of a Caged Photolabile Acetylcholine Receptor Ligand," *Biochemistry* 28:49-55 (1989)) was successfully used in such investigations to cage the different neurotransmitters that activate different receptors, carbamoylcholine (a stable analogue of acetylcholine) (Milburn et al., "Synthesis, Photochemistry, and Biological Activity of a Caged Photolabile Acetylcholine Receptor Ligand," *Biochemistry* 28:49-55 (1989)), N-methyl-D-aspartic acid (Gee et al., "Caged Bioactive Carboxylates. Synthesis, Photolysis Studies, and Biological Characterization of a New Caged N-Methyl-D-Aspartic Acid," *J Org Chem* 60:4260-4263 (1995)), kainate (Niu et al., "Synthesis and Photochemical Properties of a Kainate Precursor and Activation of Kainate and AMPA Receptor Channels on a Microsecond Time Scale," *Biochemistry* 35:2030-2036 (1996)), γ-aminobutyric acid (Wieboldt et al., "Synthesis and Photochemistry of Photolabile Derivatives of Gamma-Aminobutyric Acid for Chemical Kinetic Investigations of the Gamma-Aminobutyric Acid Receptor in the Millisecond Time Region," *Biochemistry* 33:1526-1533 (1994); Gee et al., "Synthesis and Photochemistry of a New Photolabile Derivative of GABA—Neurotransmitter Release and Receptor Activation in the Microsecond Time Region," *J Am Chem Soc* 116:8366-8367 (1994)), glutamate (Wieboldt et al., "Photolabile Precursors of Glutamate: Synthesis, Photochemical Properties, and Activation of Glutamate Receptors on a Microsecond Time Scale," *Proc Natl Acad Sci USA* 91:8752-8756 (1994)), glycine (Grewer et al., "A New Photolabile Precursor of Glycine With Improved Properties: A Tool for Chemical Kinetic Investigations of the Glycine Receptor," *Biochemistry* 39:2063-2070 (2000)), and serotonin (Breitinger et al., "Synthesis and Characterization of Photolabile Derivatives of Serotonin for Chemical Kinetic Investigations of the Serotonin 5-HT$_{(3)}$ Receptor," *Biochemistry* 39:5500-5508 (2000)). All these compounds are photolyzed in the μs-ms time region and with adequate quantum yield (Hess et al., "Development and Application of Caged Ligands for Neurotransmitter Receptors in Transient Kinetic and Neuronal Circuit Mapping Studies," *Methods Enzymol* 291:443-473 (1998); Gee et al., "Synthesis, Photochemistry, and Biological Characterization of Photolabile Protecting Groups for Carboxylic Acids and Neurotransmitters," *Methods Enzymol* 291:30-50 (1998)). This and other caging groups for neurotransmitters (Gee et al., "Desyl Esters of Amino Acid Neurotransmitters. Phototriggers for Biologically Active Neurotransmitters," *J Org Chem* 61:1228-1233 (1996); Sheehan et al., "Photolysis of Desyl Compounds. A New Photolytic Cyclization," *J Am Chem Soc* 86:5277-5281 (1964); Kuzmic et al., "Photochemical Hydrolysis of Some Nitrophenyl Acetates," *Collect Czech Chem Commun* 51:1293-1300 (1986); Ramesh et al., "Photolysis of a Protecting Group for the Carboxyl Function of Neurotransmitters Within 3 Microseconds and With Product Quantum Yield of 0.2," *Proc Natl Acad Sci USA* 90:11074-11078 (1993)) absorb only in the UV wavelength region and require expensive lasers and special rooms in which the instruments must be housed for safety reasons. Because of potential damage to the receptor-containing cells by prolonged exposure to UV light, only a few measurements can be made with each cell. Compounds that are photolyzed in the UV wavelength region can also be photolyzed by multiphoton excitation in the visible wavelength region (Denk et al., "Two-Photon Laser Scanning Fluorescence Microscopy," *Science* 248:73-76 (1990); Fedoryak et al., "Brominated Hydroxyquinoline as a Photolabile Protecting Group With Sensitivity to Multiphoton Excitation," *Org Lett* 4:3419-3422 (2000)). Uncaging, however, occurs only at the focus of the laser beam (Denk et al., "Two-Photon Laser Scanning Fluorescence Microscopy," *Science* 248:73-76 (1990); Fedoryak et al., "Brominated Hydroxyquinoline as a Photolabile Protecting Group With Sensitivity to Multiphoton Excitation," *Org Lett* 4:3419-3422 (2000)). The technique is, therefore, suitable for locating the position of a particular receptor in biological membranes, but not for activating sufficient receptors for transient kinetic measurements (Hess et al., "Development and Application of Caged Ligands for Neurotransmitter Receptors in Transient Kinetic and Neuronal Circuit Mapping Studies," *Methods Enzymol* 291:443-473 (1998)). All these problems can be avoided by use of a photolabile protecting group for neurotransmitters that can be photolyzed in the visible wavelength region.

Many organic molecules suitable for caging absorb in the visible wavelength region (Pillai V., "Photolytic Deprotection and Activation of Functional Group," *Org Photochem* 9:225-317 (1987); Bochet C., "Photolabile Protecting Groups and Linkers," *J Chem Soc, Perkin Trans* 1:125-142 (2002); Singh et al., "Synthesis and Photochemical Properties of Nitro-Naphthyl Chromophore and the Corresponding Immunoglobulin Bioconjugate," *Bioconjugate Chem* 13:1286-1291 (2002); Mizuta et al., "Design, Synthesis, Photochemical Properties and Cytotoxic Activities of Water-Soluble Caged L-Leucyl-L-Leucine Methyl Esters That Control Apoptosis of Immune Cells," *Bioorg Med Chem* 10:675-683 (2002); Furuta et al., "Brominated 7-Hydroxycoumarin-4-ylmethyls: Photolabile Protecting Groups With Biologically Useful Cross-Sections for Two Photon Photolysis," *Proc Natl Acad Sci, USA* 96:1193-1200 (1999); Xu et al., "Multiphoton Fluorescence Excitation: New Spectral Windows for Biological Nonlinear Microscopy," *Proc Natl Acad Sci USA* 93:10763-10768 (1996)). However, they have negligible or no solubility in aqueous medium (Singh et al., "Synthesis and Photochemical Properties of Nitro-Naphthyl Chromophore and the Corresponding Immunoglobulin Bioconjugate," *Bioconjugate Chem* 13:1286-1291 (2002); Mizuta et al., "Design, Synthesis, Photochemical Properties and Cytotoxic Activities of Water-Soluble Caged L-Leucyl-L-Leucine Methyl Esters That Control Apoptosis of Immune Cells," *Bioorg Med Chem* 10:675-683 (2002); Furuta et al., "Brominated 7-Hydroxy-coumarin-4-Ylmethyls: Photolabile Protecting Groups With Biologically Useful Cross-Sections for Two Photon Photolysis," *Proc Natl Acad Sci, USA* 96:1193-1200 (1999); Xu et al., "Multiphoton Fluorescence Excitation New Spectral Windows for Biological Nonlinear Microscopy," *Proc Natl Acad Sci USA* 93:10763-10768 (1996)). Recently, the substituted 2-nitroveratrole group (Bochet C., "Orthogonal Photolysis of Protecting Groups," *Angew Chem, Int Ed* 40:2071-2073 (2001)), nitroindolines (Canepari et al., "Photochemical and Pharmacological Evaluation of 7-Nitroindolinyl-and 4-Methoxy-7-Nitroindolinyl-Amino Acids as Novel, Fast Caged Neurotransmitters," *J Neurosci Methods* 112:29-42 (2001)), the phenacyl group (Banerjee et al., "Protecting Group Release Through Photoinduced Electron Transfer: Wavelength Control Through Sensitized Irradiation," *Tetrahedron Lett* 39:4635-4638 (1998)), and substituted coumarins (Furuta et al., "Brominated 7-Hydroxycoumarin-4-ylmethyls: Photolabile Protecting Groups With Biologically Useful Cross-Sections for Two Photon Photolysis," *Proc Natl Acad Sci, USA* 96:1193-1200 (1999); Lin et al., "A Strategy for the Construction of Caged Diols Using a Photolabile Protecting Group," *J Org Chem* 67:2723-2726 (2002); Hagen et al., "Highly Efficient and Ultrafast Phototriggers for cAMP and cGMP by Using Long-Wavelength UV/Vis-Activation," *Angew Chem, Int Ed* 40:1045-1048 (2001); Takaoka et al., "Synthesis and Photoreactivity of Caged Blockers for Glutamate Transporters," *Bioorg Med Chem Lett* 13:965-970 (2003); Takaoka et al., "Synthesis of Carbamate-Type Caged Derivatives of a Novel Glutamate Transporter Blocker," *Bioorg Med Chem* 12:3687-3694 (2004)) have been studied as caging groups that can be deprotected by visible light. However, many of these compounds have undesirable properties limiting their usefulness, such as low solubility in aqueous medium and/or slow photolysis (Takaoka et al., "Synthesis of Carbamate-Type Caged Derivatives of a Novel Glutamate Transporter Blocker," *Bioorg Med Chem* 12:3687-3694 (2004)), and are, therefore, unsuitable for transient kinetic investigations of membrane-bound proteins on cell surfaces. In the case of the 2-nitroveratrole group, the rate of release of the bioactive compound (Bochet C., "Wavelength-Selective Cleavage of Photolabile Protecting Groups," *Tetrahedron Lett* 41:6341-6346 (2000)) is slow, in the minutes region. Various coumarin derivatives are stable and/or soluble in DMSO solutions (Takaoka et al., "Synthesis and Photoreactivity of Caged Blockers for Glutamate Transporters," *Bioorg Med Chem Lett* 13:965-970 (2003). Aqueous solubility is required to investigate membrane-bound proteins. The stability of caged compounds in aqueous medium is also important, because contamination of the receptors with free neurotransmitter while they equilibrate with the caged compound interferes with the kinetic measurements.

All the following characteristics are required for the caged compound to be useful in transient kinetic investigation of neurotransmitter receptors on cell surfaces.
(1) The compound must be soluble and stable in water at physiological pH.
(2) The release of bioactive compound should be sufficiently fast (in the microsecond time scale) so that release of neurotransmitter does not become the rate-determining step.
(3) The photolysis process should have sufficient quantum yield so that the bioactive compound is released in high enough concentration for kinetic measurements.
(4) Both the caged compound and the photolysis byproducts must be biologically inert.
(5) The caged compound should be photolyzed in the visible wavelength region in order to allow more measurements to be made with each cell because photodamage to the cell or the receptors is avoided. Much less expensive and simple-to-use light sources are available for experiments in the visible wavelength region, thereby opening up this important field to an increasing number of investigators.

Transient kinetic measurements with each cell require two control experiments. A standard concentration of neurotransmitter is applied to the cell at the beginning of the experiment, using the cell-flow technique (Udgaonkar et al., "Chemical Kinetic Measurements of a Mammalian Acetylcholine Receptor by a Fast-Reaction Technique," *Proc Natl Acad Sci USA* 84:8758-8762 (1987)). Although the cell-flow technique has a considerably poorer time resolution (~10 ms) than the laser-pulse photolysis technique (~50 µs) (Milburn et al., "Synthesis, Photochemistry, and Biological Activity of a Caged Photolabile Acetylcholine Receptor Ligand," *Biochemistry* 28:49-55 (1989); Hess et al., "Development and Application of Caged Ligands for Neurotransmitter Receptors in Transient Kinetic and Neuronal Circuit Mapping Studies," *Methods Enzymol* 291:443-473 (1998)), it can be used to calculate the amount of neurotransmitter that is released from the caged compound in the kinetic measurements (Udgaonkar et al., "Chemical Kinetic Measurements of a Mammalian Acetylcholine Receptor by a Fast-Reaction Technique," *Proc Natl Acad Sci USA* 84:8758-8762 (1987)). This measurement, with the same standard concentration of the neurotransmitter, is repeated at the end of the laser-pulse photolysis measurement to assess possible damage to the receptors or the cell during the experiment. Additionally, obtaining a good seal between the recording electrode and a cell is time-consuming. The ability to make many kinetic measurements with each cell has, therefore, many advantages, including a reduction in the experimental error. It is, therefore, a necessity that the caged neurotransmitter is stable in water during the time it takes to make the measurements with a cell.

(Coumarin-4-yl)methyl derivatives are newly developed caging groups that have been successfully applied to protect biological activity in phosphates (Givens et al., "Photochemistry of Phosphate Esters: An Efficient Method for the Generation of Electrophiles," *J. Am. Chem. Soc.* 106:6860-6861 (1984); Furuta et al., "Photochemical Properties of New Photolabile cAMP Derivatives in a Physiological Saline Solution," *J. Org. Chem.* 60:3953-3956 (1995); Hagen et al., "Synthesis, Photochemistry and Application of (7-Methoxycoumarin-4-yl)Methyl-Caged 8-Bromoadenosine Cyclic 3',5'-Monophosphate and 8-Bromoguanosine Cyclic 3',5'-Monophosphate Photolyzed in the Nanosecond Time Region," *J Photochem. Photobiol., B* 53:91-102 (1999); Hagen et al., "Highly Efficient and Ultrafast Phototriggers for cAMP and cGMP by Using Long-Wavelength UV/Vis-Activation," *Angew Chem, Int Ed* 40:1045-1048 (2001); Geissler et al., "DMACM-Caged Adenosine Nucleotides Ultrafast Phototriggers for ATP, ADP, and AMP Activated by Long-Wavelength Irradiation," *Chem Bio Chem* 4:162-170 (2003); Geissler et al., "(Coumarin-4-yl)Methyl Esters as Highly Efficient, Ultrafast Phototriggers for Proton and Their Application to Acidifying Membrane Surfaces," *Angew. Chem. Int. Ed.* 44:1195-1198 (2005)), carboxylates (Furuta et al., "Brominated 7-Hydroxycoumarin-4-ylmethyls: Photolabile Protecting Groups With Biologically Useful Cross-Sections for Two Photon Photolysis," *Proc Natl Acad Sci, USA* 96:1193-1200 (1999)), sulfates (Geissler et al., "(Coumarin-4-yl)Methyl Esters as Highly Efficient, Ultrafast Phototriggers for Proton and Their Application to Acidifying Membrane Surfaces," *Angew. Chem. Int. Ed.* 44:1195-1198 (2005)), sulfonates (Geissler et al., "(Coumarin-4-yl)Methyl Esters as Highly Efficient, Ultrafast Phototriggers for Proton and Their Application to Acidifying Membrane Surfaces," *Angew. Chem. Int. Ed.* 44:1195-1198 (2005)), diols (Lin et al., "A Strategy for the Construction of Caged Diols Using a Photolabile Protecting Group," *J Org Chem* 67:2723-2726 (2002)), alcohols (Suzuki et al., "Coumarin-4-ylmethoxycarbonyls as Phototriggers for Alcohols and Phenols," *Organic Letters* 5:4867-4870 (2003)), and carbonyl compounds (Lu et al., "Bhc-diol as a Photolabile Protecting Group for Aldehydes and Ketones," *Org. Lett.* 5:2119-2122 (2003)). Amino and hydroxyl functionalities have also been protected via carbamate (Furuta et al., "Brominated 7-Hydroxycoumarin-4-ylmethyls: Photolabile Protecting Groups With Biologically Useful Cross-Sections for Two Photon Photolysis," *Proc Natl Acad Sci, USA* 96:1193-1200 (1999)) or carbonate (Suzuki et al., "Coumarin-4-ylmethoxycarbonyls as Phototriggers for Alcohols and Phenols," *Org. Lett.* 5:4867-4870 (2003)) linkers.

7-N,N-Diethylamino-4-hydroxymethyl coumarin (DECM) has been used to cage nucleotides such as ADP and ATP. The DECM-caged nucleotides were photolyzed in the 300-400 nm wavelength region (Hagen et al., "[7-(Dialkylamino)Coumarin-4-yl]Methyl-Caged Compounds as Ultrafast and Effective Long-Wavelength Phototriggers of 8-Bromo-Substituted Cyclic Nucleotides," *Chem Bio Chem* 4:434-442 (2003)). However, it is unknown if this caging group can be used with carboxylic acids, and whether the quantum yield and rate of photolysis in the visible wavelength region would be sufficient (Hess et al., "Development and Application of Caged Ligands for Neurotransmitter Receptors in Transient Kinetic and Neuronal Circuit Mapping Studies," *Methods Enzymol: Caged Compd* 291:443-473 (1998)) for transient kinetic measurements.

The present invention is directed to overcoming these deficiencies in the art.

SUMMARY OF THE INVENTION

The present invention relates to a photolabile compound including a coumarin family caging group covalently bound to an organic moiety containing a carboxyl group, an amino group, a sulfhydryl group, and/or a hydroxyl group. The photolabile compound, upon absorbing visible light, releases the organic moiety.

Another aspect of the present invention relates to a method of making a photolabile compound that releases a biologically active compound upon absorbing visible light. The method involves providing an organic moiety containing a carboxyl group, an amino group, a sulfhydryl group, and/or a hydroxyl group. Then, a coumarin family caging group is bound to the organic moiety under conditions effective to make a photolabile compound.

The present invention also relates to a method of obtaining a biologically active compound in a sample. The method involves adding to a sample a photolabile compound including a coumarin family caging group covalently bound to an organic moiety containing a carboxyl group, an amino group, a sulfhydryl group, and/or a hydroxyl group. The sample is then illuminated with visible light under conditions effective to obtain a biologically active compound including the organic moiety.

The present application discloses a photolabile protecting (caging) group that is new for carboxylic acids and is suitable for investigating the fast biological reactions mediated by cell surface receptors (Schmidt et al., "Kinetics Study of the Photocleavage of (Coumarin-4-yl)methyl Esters," *J. Phys. Chem. A* 109:5000-5004 (2005), which is hereby incorporated by reference in its entirety). Unlike previously used caging groups for carboxylic acids, it can be photolyzed rapidly and efficiently in the visible wavelength region in the microsecond-to-millisecond time region.

The present application discloses using caging group 7-N,N-diethyl aminocoumarin (DECM) to cage the γ-carboxyl group of glutamic acid, which is also a neurotransmitter. The caged compound has a major absorption band with a maximum at 390 nm ($\epsilon_{390}$=13651 M$^{-1}$ cm$^{-1}$). Experiments were performed at 400 nm ($\epsilon_{400}$=12232 M$^{-1}$ cm$^{-1}$) and longer wavelengths. DECM-caged glutamate was water soluble and stable at pH 7.4 and 22° C. It photolyzed rapidly in aqueous solution to release glutamic acid within 3 μs with a quantum yield of 0.11±0.008 in the visible region. In whole-cell current-recording experiments, using HEK (human embryonic kidney)-293 cells expressing glutamate receptors and visible light for photolysis, DECM-caged glutamate and its photolytic byproducts were found to be biologically inert. The DECM caging group was also used to cage the α-carboxyl group of glycine. The caged glycine had a major absorption band with a maximum at 390 nm ($\epsilon_{390}$=13869 M$^{-1}$ cm$^{-1}$). Photolysis was performed at 400 nm and longer wavelengths ($\epsilon_{400}$=12427 M$^{-1}$ cm$^{-1}$). Under physiological conditions, DECM-caged glycine was water soluble and stable. It photolyzed rapidly in aqueous solution to release glycine within 2.6 μs, with a quantum yield of 0.12±0.009 in the visible region. The experimental results demonstrated that neither DECM-caged glycine nor its byproducts inhibited or activated the glycine receptors on the surface of HEK293 cells.

Neurotransmitter receptors that are activated by various carboxyl-group-containing compounds play a central role in signal transmission between ~10$^{12}$ neurons of the nervous system. Caged neurotransmitters have become an essential tool in transient kinetic investigations of the mechanism of action of neurotransmitter receptors. Previously uncaging the compounds suitable for transient kinetic investigations required ultraviolet light and expensive lasers, and, therefore, special precautions. The availability of caged neurotransmitters as disclosed in the present application (e.g., DECM-caged glutamate and DECM-caged glycine) and having properties suitable for transient kinetic investigations that can be photolyzed by visible light allows the use of simple-to-use, readily available inexpensive light sources such as the Rapp flash lamp, thereby opening up this important field to an increasing number of investigators.

BRIEF DESCRIPTION OF THE DRAWINGS

FIG. 1 shows the UV-vis spectrum of DECM-caged glutamate (250 μM in HEK extracellular buffer, pH 7.4, 22° C.) at times t=0 min (solid line) and t=240 min (dotted line) after the compound was dissolved. The data at t=5, 10, 20, 30, 60, and 120 min are not shown. The path length of the cuvette was 10 mm.

FIG. 7 shows the UV-vis spectrum of DECM-caged glycine (250 μM in HEK extracellular buffer, pH 7.4, 22° C.) at times t=0 min (solid line) and t=240 min (dotted line) after the compound was dissolved. The data at t=5, 10, 20, 30, 60, and 120 min are not shown. The path length of the cuvette was 10 mm.

DETAILED DESCRIPTION OF THE INVENTION

Figure 1:
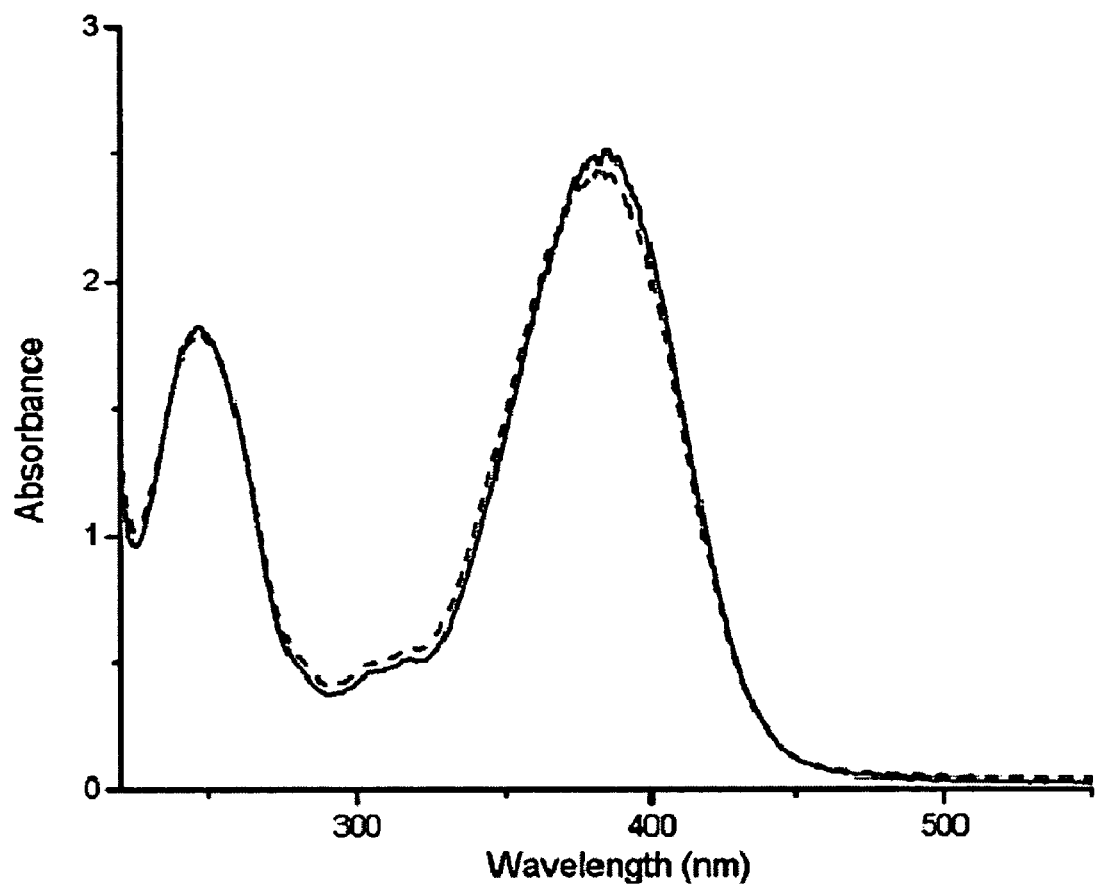
FIG. 1 illustrates the thermal hydrolysis of DECM-caged glutamate.

The present invention relates to a photolabile compound including a coumarin family caging group covalently bound to an organic moiety containing a carboxyl group, an amino group, a sulfhydryl group, and/or a hydroxyl group. The photolabile compound, upon absorbing visible light, releases the organic moiety.

In one embodiment of the present invention, the organic moiety of the photolabile compound is caged through the carboxyl group as an ester. In another embodiment of the present invention, the organic moiety of the photolabile compound is caged through the amino group, specifically through the α-nitrogen atom, as a carbamate. Alternatively, the organic moiety can be caged through a non-α-nitrogen atom (as in lysine or gammaminobutyric acid). In another embodiment of the present invention, the organic moiety of the photolabile compound is caged through the sulfhydryl group as a thioether (as in cysteine). In yet another embodiment of the present invention, the organic moiety of the photolabile compound is caged through the hydroxyl group as an ether or a carbonate of the hydroxyl group (as in serine, threonine or tyrosine).

In another embodiment of the present invention, the organic moiety of the photolabile compound is an amino acid. The amino acid may be natural or synthetic, optically active or non-optically active. Further, the amino acid can be optionally incorporated into a natural or synthetic peptide or at one or more sites in a protein. In another embodiment of the present invention, the amino acid is a neurotransmitter. Suitable amino acids which can be caged by the coumarin family caging group of the present invention include, but are not limited to, aspartic acid; gammaminobutyric acid; beta alanine; saclofen; S-sulpho-L-cysteine; γ-N-oxalyl-L-α,γ-diaminobutyric acid; O-phospho-D-serine philanthotoxin 343; (±)-cis-2,3-piperidinedicarboxylic acid; piperidine-4-sulphonic acid; L-trans-pyrrolidine-2,4-dicarboxylic acid; isoguvacine; indole-2-carboxylic acid; (+)-α-methyl-4-carboxyphenylglycine; 6-nitroquinoxaline-2,3-dione; γ-D-glutamylaminoethylphosphonic acid; D-homocysteic acid; L-homocysteinesulphinic acid; (RS)-3-hydroxyphenylglycine; 3-hydroxy-2-quinoxaline-carboxylic acid; 5-7-dichlorokynurenic acid; dihydrokainic acid; domoic acid; L-glutamic acid; (S)-4-carboxyphenylglycine; 6-chlorokynurenic acid; D-cysteic acid; L-cysteine sulphinic acid; (±)-3-carboxyphenylalanine; (R)-5-bromowillardiine; aminomalonic acid; and glycine. Other suitable protectable organic moieties which are useful in the present invention are identified in Gilman et al., "The Pharmacological Basis of Therapeutics (8th ed.)," Macmillan, New York (1990), which is hereby incorporated by reference in its entirety. Peptides may also be protected. Peptides, like proteins that are involved in all biological reactions and form important structural components of all organisms, also contain protectable functional groups. Suitable such peptides are disclosed in Patek, M., "Multistep Deprotection for Peptide Chemistry," *Int. J. Pept. Protein Res.* 42:97-117 (1993); Jung et. al., "Multiple Peptide Synthesis Methods and Their Applications," *Angew. Chem. Int. Ed. Engl.* 3:367-383 (1992); Muir et. al., "The Chemical Synthesis of Proteins," *Curr. Opin. Biotechnol.* 4:420-427 (1993); Gesellchen et. al., "Synthesis of Peptides and Proteins by Chemical and Biotechnological Means," in Lee, ed., *Advances in Parenteral Sciences*, Vol 4., Marcel Dekker, Inc.: New York, pp. 57-135 (1991); Tam et. al., "Strong Acid Deprotection of Synthetic Peptides: Mechanisms and Methods," in Udenfriend eds., *Peptides: Analysis, Synthesis, Biology, Special Methods in Peptide Synthesis*, part C, Vol. 9, Academic Press, Inc.: San Diego, p. 185-248 (1987), which are hereby incorporated by reference in their entirety.

In one embodiment of the present invention, the coumarin family caging group is 7-N,N-diethylamino-4-hydroxymethyl coumarin (DECM).

The photolabile compound of the present invention is biologically inert, is soluble and stable in water under physiological conditions. One example of the photolabile compound of the present invention is DECM-caged glutamate having the formula:

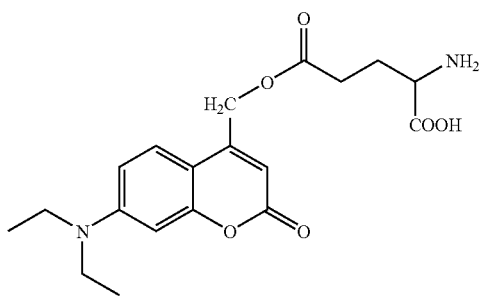

or a trifluoroacetate salt or a biologically compatible salt thereof. Another example of the photolabile compound of the present invention is DECM-caged glycine having the formula:

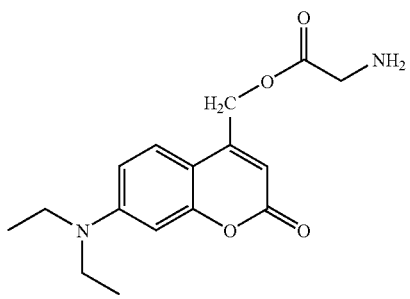

or a trifluoroacetate salt or a biologically compatible salt thereof. Another example of the photolabile compound of the present invention is DECM-caged alanine having the formula:

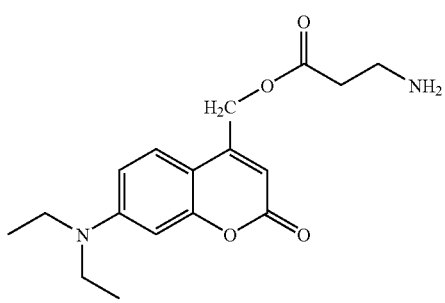

or a trifluoroacetate salt or a biologically compatible salt thereof. Yet another example of the photolabile compound of the present invention is DECM-caged gammaminobutyric acid having the formula:

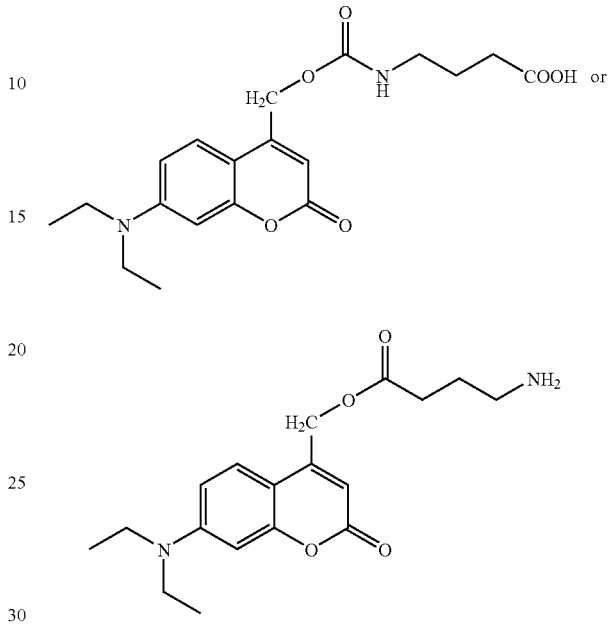

or a trifluoroacetate salt or a biologically compatible salt thereof.

Another aspect of the present invention relates to a method of making a photolabile compound that releases a biologically active compound upon absorbing visible light. The method involves providing an organic moiety containing a carboxyl group, an amino group, a sulfhydryl group, and/or a hydroxyl group. Then, a coumarin family caging group is bound to the organic moiety under conditions effective to make a photolabile compound.

In one embodiment of the present invention, the method involves providing an amino acid or an amino acid derivative dissolved in an organic solvent. Then, 7-N,N-diethylamino-4-hydroxymethyl coumarin is added to the amino acid or the amino acid derivative under conditions effective to produce a photolabile 7-N,N-diethylamino coumarin-caged amino acid compound.

In another embodiment of the present invention, the coumarin family caging group is bound to the organic moiety through the carboxyl group of the organic moiety. Schemes 1, 2, 3, and 4, shown infra, illustrate methods of making specific photolabile DECM-caged amino acids, such as DECM-caged glutamate, DECM-caged glycine, DECM-caged alanine, and DECM-caged gammaminobutyric acid. Thus, the photolabile caged compounds can be prepared by means of an esterification reaction, i.e. by reacting a carboxylic acid with a 7-N,N-diethylamino-4-hydroxymethyl coumarin, generally in the presence of one or more esterification catalysts under conventional esterification reaction conditions. Since functionalities other than carboxyl also react with coumarin groups, if such other functionality is present on the carboxylic acid then it must be blocked prior to the caging reaction. For example, for the amino acid glycine, N-t-butyloxycarbonylglycine in which the amino group is blocked by the t-butyloxycarbonyl group (t-BOC), is conveniently used. Other acid labile blocking groups for amino groups are benzyloxycarbonyl, p-methoxy benzyloxycarbonyl, triphenylmethyl, o-nitrobenzene sulfonyl, and toluene sulfonyl. Still further blocking groups can be found in Bodanszky et al., "The Practice of Peptide Synthesis," Springer Verlag (1984), which is hereby incorporated by reference in its entirety.

Suitable esterification catalysts for use in the method of the present invention include the conventional esterification catalysts such as 4-dimethylaminopyridine. To facililitate the esterification reaction, the use of a coupling agent, such as 1,3-dicyclohexylcarbodiimide (DCC), is recommended. The reaction will generally be performed in the presence of an organic solvent, such as methylene chloride.

In other embodiments of the method of the present invention, the coumarin family caging group is bound to the organic moiety through the amino group, the sulfhydryl group, or the hydroxyl group of the organic moiety.

If the caged compound contains blocked functional groups for non-carboxyl functionality, then those groups, e.g. T-BOC for amines, need to be removed without disturbing the 7-N, N-diethylamino-4-hydroxymethyl coumarin caging group. One technique for removing t-BOC from caged amino acids is the trifluoroacetic acid hydrolysis as described in Schemes 1-4 shown infra. Other suitable techniques include the use of a combination of anhydrous ethyl acetate and hydrogen chloride. catalytic hydrogenation, deprotection with hydrogen fluoride, or hydrobromic acid in acetic acid or in trifluoroacetic acid.

The photolabile compounds of the present invention can be photolysed to cleave the coumarin family caging group and release a biologically active compound, as illustrated in Schemes 1-4. Thus, the present invention also relates to a method of obtaining a biologically active compound in a sample. The method involves adding to a sample a photolabile compound including a coumarin family caging group covalently bound to an organic moiety containing a carboxyl group, an amino group, a sulfhydryl group, and/or a hydroxyl group. The sample is then illuminated with visible light under conditions effective to obtain a biologically active compound including the organic moiety.

A biologically active compound, as used herein, is a natural molecule that is found naturally in living systems such as animals or plants, or is a synthetic molecule that would elicit a biological response in a living organism. This response may be essentially immediate, such as an effect on the conformation, bonding, binding, electrical, or osmotic properties of a cell, tissue, organ or organism.

The sample is typically illuminated with visible light at a wavelength greater than about 400 nm and less than about 450 nm. Suitable light sources that can be used include flash lamps and lasers.

In another embodiment of the present invention, the sample is illuminated with visible light under conditions to release the biologically active compound containing the organic moiety from the photolabile compound within a period of less than about 1 ms. In another embodiment of the present invention, the sample is illuminated with visible light under conditions to release the biologically active compound containing the organic moiety from the photolabile compound at a quantum yield of at least about 0.1. Typically, the sample includes cells.

The photolabile caged compounds of the present invention are photolysed in a biological system to yield a biologically active or fluorescent photoproduct in situ to allow rapid but controlled release of the biologically active product to initiate or block intracellular function and analyze the biological system, e.g., to study the dynamics of the biological system, intercellular communication, cell or tissue development, intracellular structure, transport across membranes, etc. Thus, in one embodiment of the present invention, the biologically active compound is a neurotransmitter and is used for kinetically investigating neurotransmitter-receptor interactions on the surface of a cell in the microsecond to millisecond time domain (see Hess G., "Photochemical Release of Neurotransmitters—Transient Kinetic Investigations of Membrane-Bound Receptors on the Surface of Cells in the Microsecond-To-Millisecond Time Region," in Goeldner, eds., *Dynamic Studies in Biology Phototriggers, Photoswitches and Caged Biomolecules* Chapter 4.3 (Wiley) (2005); Hess G., "Rapid Chemical Reaction Techniques Developed for Use in Investigations of Membrane-Bound Proteins (Neurotransmitter Receptors), *Biophysical Chemistry* 100:493-506 (2003); Hess G., "Design and Application of Caged Neurotransmitters," in Yuste, eds., *Imaging Living Cells*, Cold Spring Harbor Press: Cold Spring Harbor, N.Y., pp. 25.1-25.18 (1999); Gee et al., "Synthesis, Photochemistry and Biological Characterization of Photolabile Protecting Groups for Carboxylic Acids and Neurotransmitters," *Methods in Enzymology* 291:30-50 (1998); Hess et al., "Development and Application of Caged Ligands for Neurotransmitter Receptors in Transient Kinetic and Neuronal Circuit Mapping Studies," *Methods in Enzymology* 291:443-473 (1998), which are hereby incorporated by reference in their entirety). In another embodiment of the present invention, the biologically active compound is a neurotransmitter and is used for spatially locating neurotransmitter receptors on a cell or tissue slices (see Hess et al., "Development and Application of Caged Ligands for Neurotransmitter Receptors in Transient Kinetic and Neuronal Circuit Mapping Studies," *Methods in Enzymology* 291:443-473 (1998); Hess G., "Design and Application of Caged Neurotransmitters," in Yuste, eds., *Imaging Living Cells*, Cold Spring Harbor Press: Cold Spring Harbor, N.Y., pp. 25.1-25.18 (1999); Li et al., "Identification of Chemical Synapses in the Pharynx of *Caenorhabditis elegans*," *Proc Natl Acad Sci USA* 94:5912-5916 (1997), which is hereby incorporated by reference in its entirety).

EXAMPLES

The following examples are provided to illustrate embodiments of the present invention but are by no means intended to limit its scope.

Example 1

Synthesis of DECM-Caged Glutamate

All the starting materials were procured from Aldrich (Milwaukee, Mich.). Scheme 1 below shows all synthetic reactions for making DECM-caged glutamate, as well as the mechanism of photolysis of DECM-caged glutamate.

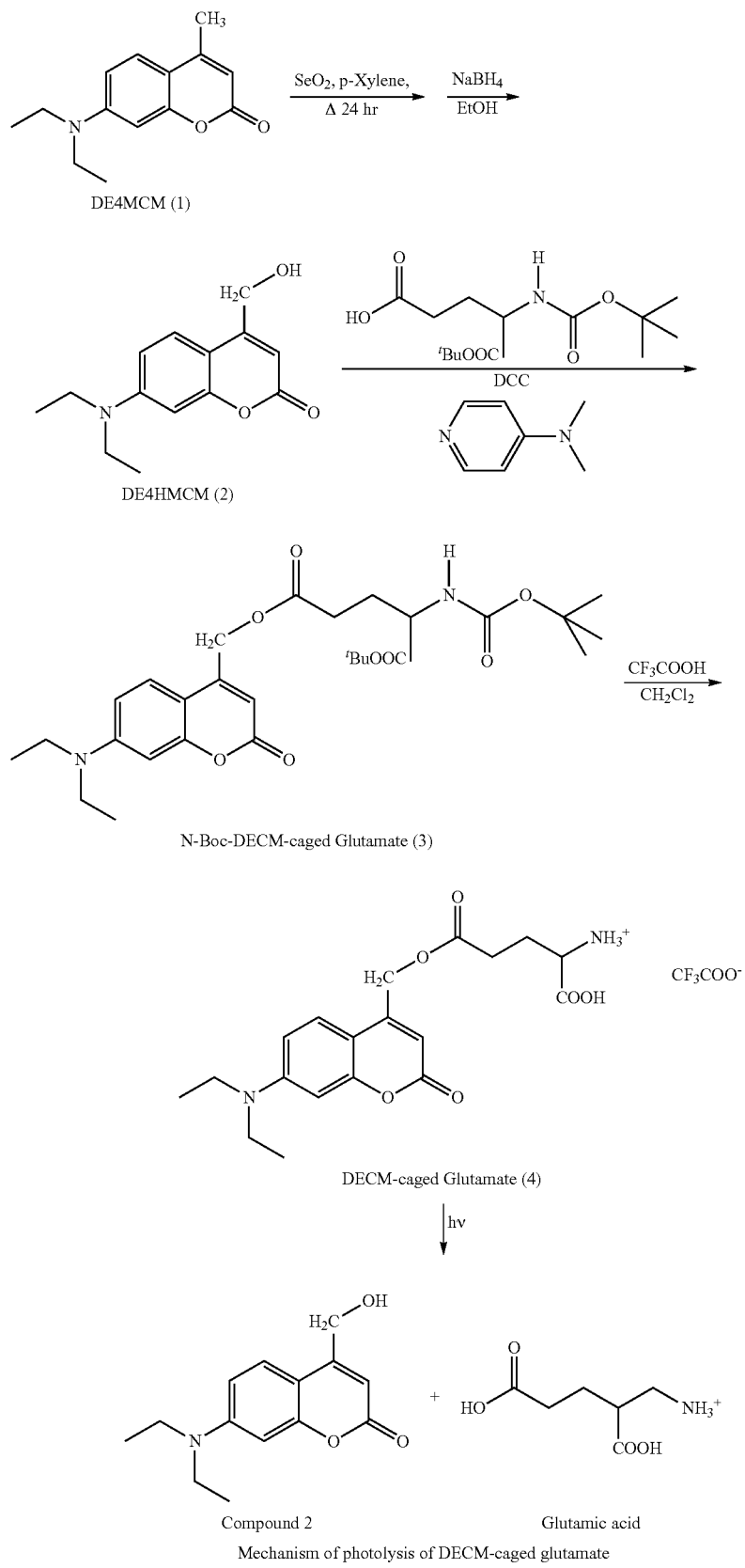
Scheme 1
DE4MCM (1)
DE4HMCM (2)
N-Boc-DECM-caged Glutamate (3)
DECM-caged Glutamate (4)
Compound 2       Glutamic acid
Mechanism of photolysis of DECM-caged glutamate

7-N,N-Diethylamino-4-hydroxymethylcoumarin (2)

7-N,N-Diethylamino-4-hydroxymethylcoumarin 2 was synthesized as previously described in Hagen et al., "[7-(Dialkylamino)Coumarin-4-yl]Methyl-Caged Compounds as Ultrafast and Effective Long-Wavelength Phototriggers of 8-Bromo-Substituted Cyclic Nucleotides," *Chem Bio Chem* 4:434-442 (2003), which is hereby incorporated by reference in its entirety. To a solution of 4-methyl-7-N,N-diethylaminocoumarin 1 (2.32 g, 10.0 mmol) in p-xylene (60 mL), selenium dioxide (1.66 g, 15.0 mmol) was added. This reaction mixture was heated under reflux with vigorous stirring. After 24 h, the mixture was filtered and concentrated under reduced pressure. The dark brown residual oil was dissolved in ethanol (65 mL), sodium borohydride (190 mg, 5.0 mmol) was added, and the solution was stirred for 4 h at room temperature. The suspension was carefully hydrolyzed with 1 M HCl (10 mL), diluted with $H_2O$, and extracted three times with 20 mL $CH_2Cl_2$. The organic phase was washed with $H_2O$ and brine, dried over $MgSO_4$, and concentrated in vacuo. By flash chromatography (FC) ($CH_2Cl_2$/acetone 5:1) 1.20 g (4.48 mmol, 50%) of alcohol 2 was obtained as a yellow solid: $R_f$ 0.27 (hexane/EtOAc 1:2).

$^1$H NMR (300 MHz, $CDCl_3$): δ 7.30 (d, J=9.0 Hz, 1H), 6.55 (dd, J=9.0, 2.6 Hz, 1H), 6.46 (d, J=2.6 Hz, 1H), 6.27 (t, J=1.3 Hz, 1H), 4.82 (d, J=1.3 Hz, 2H), 3.39 (q, J=7.1 Hz, 4H), 3.12 (s, 1H), 1.19 (t, J=7.1 Hz, 6H).

(7-N,N-Diethylaminocoumarin-4-yl)-methyl-N-t-BOC-glutamate (3)

N-t-BOC-L-glutamic acid-γ-butyl ester (2.751 g, 9.069 mmol), 4-dimethylaminopyridine (DMAP) (93.48 mg, 0.765 mmol), and 1,3-dicyclohexylcarbodiimide (DCC) (2.047 g, 9.92 mmol) in 100 mL of $CH_2Cl_2$ were stirred at room temperature for about 10 min. 0.7 g (2.834 mmol) of 2 was added to the reaction mixture, and the resulting mixture was stirred at room temperature in the dark for about 30 min. The reaction mixture was filtered and the solvent evaporated to give a yellow solid. The crude product was purified over a silica gel column by FC (10% acetone: $CH_2Cl_2$) to yield 1.282 g (2.41 mmol, 85%).

$^1$H NMR (300 MHz, $CDCl_3$): δ 7.27 (d, J=9.0 Hz, 1H), 6.57 (dd, J=9.0, 2.6 Hz, 1H), 6.48 (d, J=2.6 Hz, 1H), 6.1 (s, 1H), 5.2 (s, 2H), 5.08 (d, J=8 Hz, 1H), 4.25 (m, 1H), 3.39 (q, J=7.1 Hz, 4H), 2.4-2.6 (m, 2H), 2.24 (m, 1H), 1.96 (m, 1H), 1.45 (s, 9H) 1.41 (s, 9H), 1.19 (t, J=7.1 Hz, 6H).

(7-N,N-Diethylaminocoumarin-4-yl)-methyl-glutamate-trifluoroacetate (4)

(7-N,N-Diethylamino coumarin-4-yl)-methyl-N-t-BOC-glutamate (0.250 g, 0.47 mmol) was dissolved in 100 mL of dichloromethane, and the reaction mixture was cooled to 0° C. Trifluoroacetic acid (5 mL) was added slowly, and the resulting solution was stirred in the dark for about 24 h, bringing it to room temperature. The solvent was removed under reduced pressure. The residue was purified over a Sephadex (Amersham Biosciences, Piscataway, N.J.) LH-20 column with water as the eluent.

$^1$H NMR (400 MHz, $D_2O$): δ 7.7 (d, J=9.0 Hz, 1H), 7.35 (d, J=2.1 Hz, 1H), 7.27 (dd, J=9.0, 2.6 Hz, 1H), 6.42 (s, 1H), 5.27 (s, 2H), 3.83 (t, J=7.1 Hz, 1H), 3.5 (q, J=7.1 Hz, 4H), 2.62 (dt, J=7.1, 2.1 Hz, 2H), 2.1 (dq, J=7.1, 2.1 Hz, 2H), 0.97 (t, J=7.1 Hz, 6H). Anal. Calcd for $C_{21}H_{25}N_2O_8F_3$: C, 51.42; H, 5.13; N, 5.71. Found: C, 51.21; H, 5.39; N, 5.49.

Example 2

Synthesis of DECM-Caged Glycine

All the starting materials were procured from Aldrich. Scheme 2 below shows all synthetic reactions for making DECM-caged glycine, as well as the mechanism of photolysis of DECM-caged glycine.

Scheme 2

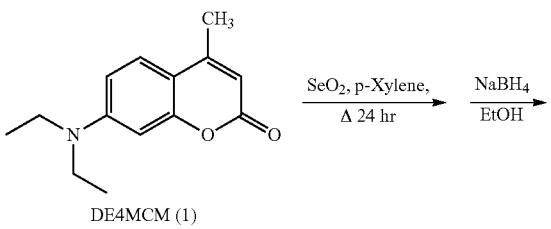

DE4MCM (1)

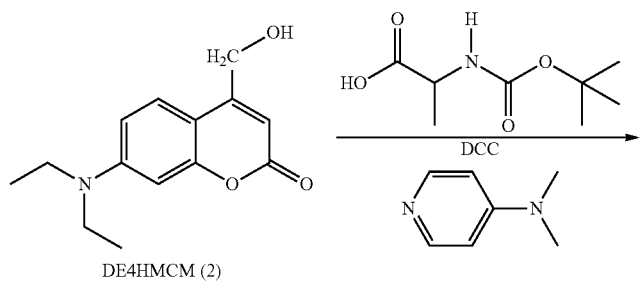

DE4HMCM (2)

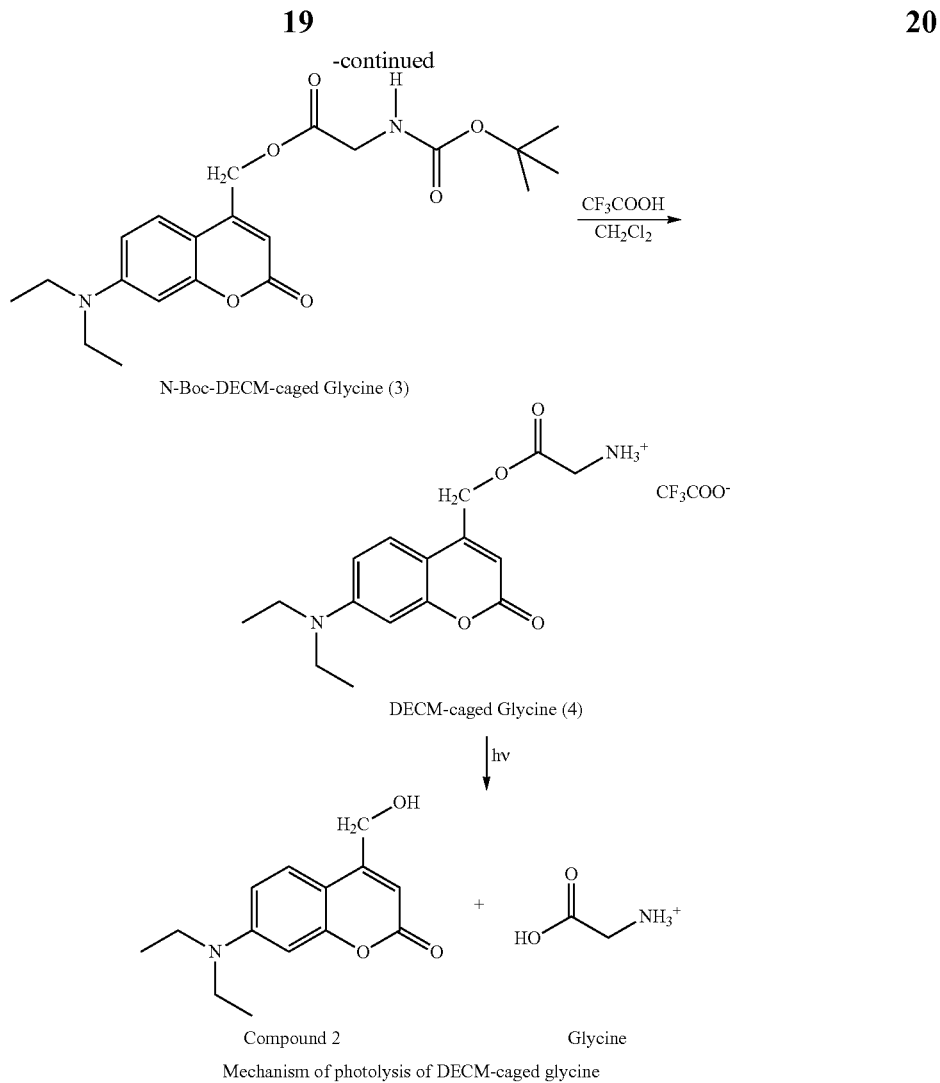

Mechanism of photolysis of DECM-caged glycine

7-N,N-Diethylamino-4-hydroxymethylcoumarin (2)

7-N,N-Diethylamino-4-hydroxymethylcoumarin 2 was synthesized as described above in Example 1.

(7-N,N-Diethylaminocoumarin-4-yl)-methyl-N-t-BOC-glycine ester (3)

N-t-BOC-glycine (998.5 mg, 5.7 mmol), 4-dimethylaminopyridine (DMAP) (58.64 mg, 0.48 mmol), and 1,3-dicyclohexylcarbodiimide (DCC) (1.285 g, 6.23 mmol) in 100 ml $CH_2Cl_2$ were stirred at room temperature for about 10 minutes. 440 mg (1.78 mmol) of 2 was added to the reaction mixture, and the resulting mixture was stirred at room temperature in the dark for about 4 h. The reaction mixture was filtered and the solvent evaporated to give a yellow solid. The crude product was purified over a silica gel column by FC (10% acetone: $CH_2Cl_2$) to yield 0.647 g (1.6 mmol, 89%).

$^1$H NMR (300 MHz, $CDCl_3$) δ 7.28 (d, J=9.0 Hz, 1H), 6.58 (dd, J=9.0, 2.6 Hz, 1H), 6.49 (d, J=2.6 Hz, 1H), 6.15 (s, 1H), 5.2 (s, 2H), 3.35 (q, J=7.1 Hz, 4H), 2.4-2.6 (m, 2H), 1.45 (s, 9H), 1.17 (t, J=7.1 Hz, 6H)

(7-N,N-Diethylaminocoumarin-4-yl)-methyl-glycine-trifluoroacetate (4)

(7-Diethylamino coumarin-4-yl)-methyl-N-t-BOC-glycine (0.2 g, 0.49 mmol) was dissolved in 100 mL of dichloromethane and the reaction mixture was cooled to 0° C. Trifluoroacetic acid (5 mL) was added slowly and the resulting solution was stirred in the dark for about 24 h, bringing it to room temperature. The solvent was removed under reduced pressure. The residue was purified over a Sephadex LH-20 column with water as the eluent.

$^1$H NMR (300 MHz, $D_2O$) δ 7.63 (d, J=9.0 Hz, 1H), 7.20 (d, J=2.1 Hz, 1H), 7.15 (dd, J=9.0, 2.6 Hz, 1H), 6.38 (s, 1H), 5.42 (s, 2H), 3.96 (s, 2H) 3.48 (q, J=7.1 Hz, 4H), 0.98 (t, J=7.1 Hz, 6H); Anal. Calcd for $C_{18}H_{21}N_2O_6F_3$: C, 51.68; H, 5.03; N, 6.7. Found: C, 51.42; H, 5.29; N, 6.49.

Example 3

Synthesis of DECM-Caged Alanine

All the starting materials were procured from Aldrich. Scheme 3 below shows all synthetic reactions for making DECM-caged alanine, as well as the mechanism of photolysis of DECM-caged alanine.

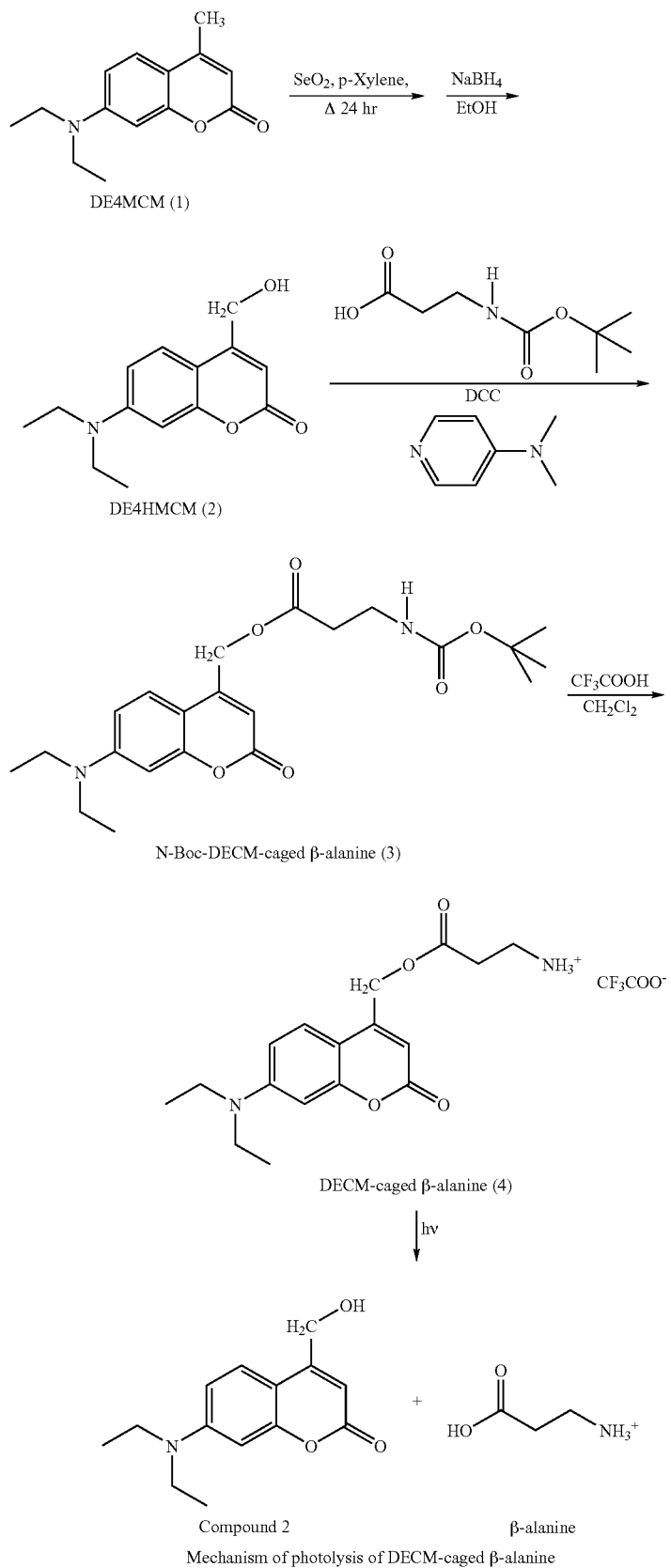

7-N,N-Diethylamino-4-hydroxymethylcoumarin (2)

7-N,N-Diethylamino-4-hydroxymethylcoumarin 2 was synthesized as described above in Example 1.

(7-N,N-Diethylaminocoumarin-4-yl)-methyl-N-t-BOC-alanine ester (3)

N-t-BOC-β-alanine (1.716 g, 9.069 mmol), 4-dimethylaminopyridine (DMAP) (93.48 mg, 0.765 mmol), and 1,3-dicyclohexylcarbodiimide (DCC) (2.047 g, 9.92 mmol) in 100 ml $CH_2Cl_2$ were stirred at room temperature for about 10 minutes. 700 mg (2.834 mmol) of 2 was added to the reaction mixture, and the resulting mixture was stirred at room temperature in the dark for about 4 h. The reaction mixture was filtered and the solvent evaporated to give a yellow solid. The crude product was purified over a silica gel column by FC (10% acetone: $CH_2Cl_2$) to yield 1.041 g (2.41 mmol, 85%).

$^1$H NMR (300 MHz, $CDCl_3$) δ 7.25 (d, J=9.0 Hz, 1H), 6.55 (dd, J=9.0, 2.6 Hz, 1H), 6.48 (d, J=2.6 Hz, 1H), 6.07 (s, 1H), 5.2 (s, 2H), 3.4 (q, J=7.1 Hz, 4H), 2.63 (t, 2H), 1.95 (t, 2H), 1.42 (s, 9H), 1.17 (t, J=7.1 Hz, 6H).

(7-N,N-Diethylaminocoumarin-4-yl)-methyl-alanine-trifluoroacetate (4)

(7-Diethylamino coumarin-4-yl)-methyl-N-t-BOC-alanine (1.0 g, 2.32 mmol) was dissolved in 100 mL of dichloromethane and the reaction mixture was cooled to 0° C. Trifluoroacetic acid (5 mL) was added slowly and the resulting solution was stirred in the dark for about 48 h, bringing it to room temperature. The solvent was removed under reduced pressure. The residue was purified over a Sephadex LH-20 column with water as the eluent.

$^1$H NMR (300 MHz, $D_2O$) δ 7.65 (d, J=9.0 Hz, 1H), 7.42 (d, J=2.1 Hz, 1H), 7.28 (dd, J=9.0, 2.6 Hz, 1H), 6.42 (s, 1H), 5.28 (s, 2H), 3.47 (q, J=7.1 Hz, 4H), 3.15 (t, J=7.1 Hz, 2H), 2.8 (t, J=7.1 Hz, 2H), 0.97 (t, J=7.1 Hz, 6H); Anal. Calcd for $C_{19}H_{23}N_2O_6F_3$: C, 52.78; H, 5.32; N, 6.48. Found: C, 52.89; H, 5.41; N, 6.29.

Example 4

Synthesis of DECM-Caged GABA

All the starting materials were procured from Aldrich. Scheme 4 below shows all synthetic reactions for making DECM-caged GABA, as well as the mechanism of photolysis of DECM-caged GABA.

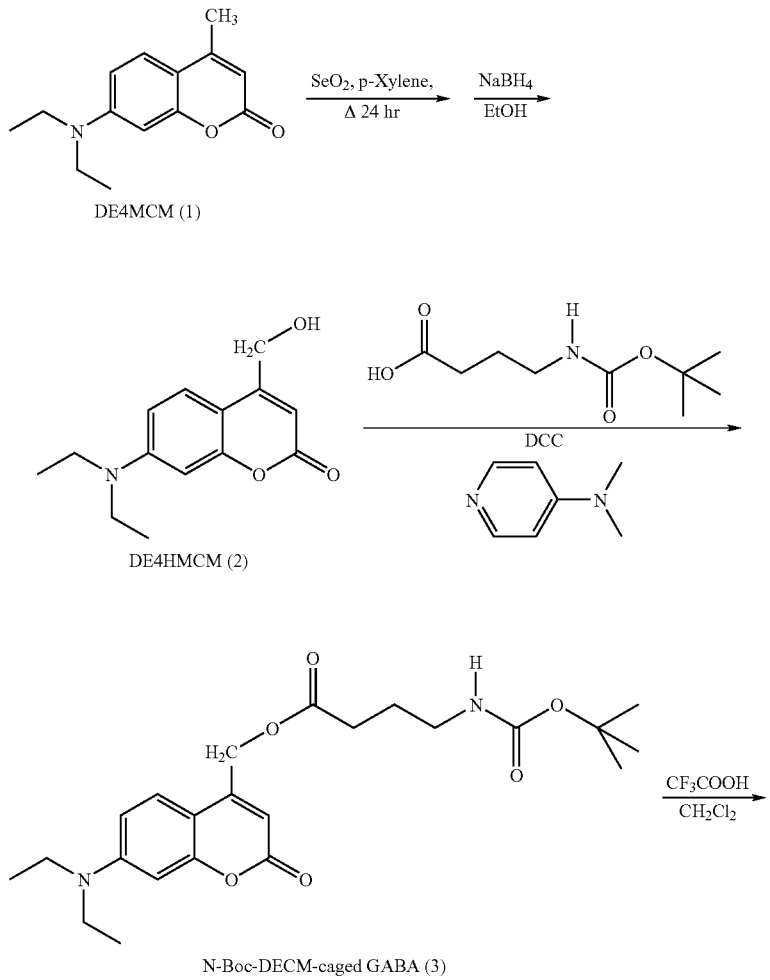

Scheme 4

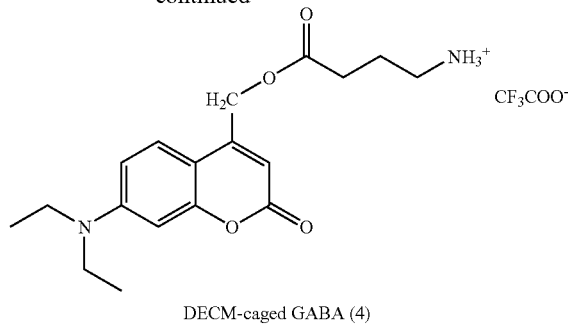

DECM-caged GABA (4)

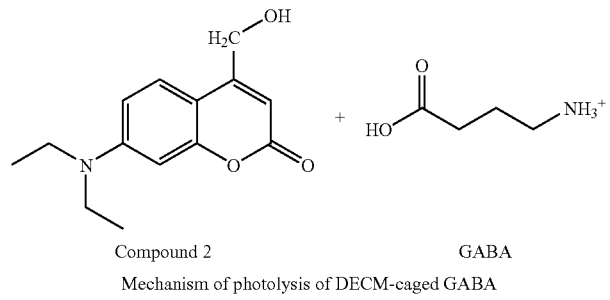

Compound 2      GABA

Mechanism of photolysis of DECM-caged GABA

7-N,N-Diethylamino-4-hydroxymethylcoumarin (2)

7-N,N-Diethylamino-4-hydroxymethylcoumarin 2 was synthesized as described above in Example 1.

(7-N,N-Diethylaminocoumarin-4-yl)-methyl-N-t-BOC-GABA ester (3)

N-t-BOC-GABA (1.661 g, 8.176 mmol), 1,3-dicyclohexylcarbodiimide (DCC) (1.845 g, 8.44 mmol) and 4-dimethylaminopyridine (DMAP) (84.28 mg, 0.689 mmol), in 25 ml $CH_2Cl_2$ were stirred at room temperature for about 10 minutes. 631 mg (2.555 mmol) of 2 dissolved in 25 ml $CH_2Cl_2$ was added to the reaction mixture and the resulting mixture was stirred at room temperature in the dark for 4 h. The reaction mixture was filtered and the solvent evaporated to give a yellow solid. The crude product was purified over silica gel column by FC (10% acetone: $CH_2Cl_2$) to yield 0.924 g (2.14 mmol, 84%).

$^1$H NMR (300 MHz, $CDCl_3$) δ 7.30 (d, J=9.0 Hz, 1H), 6.68 (dd, J=9.0, 2.6 Hz, 1H), 6.5 (d, J=2.6 Hz, 1H), 5.97 (s, 1H), 5.2 (s, 2H), 3.35 (q, J=7.1 Hz, 4H), 3.10 (t, J=7.1 Hz, 2H), 2.1 (t, J=7.1 Hz, 2H), 1.83 (m, 2H), 1.45 (s, 9H), 1.17 (t, J=7.1 Hz, 6H).

(7-N,N-Diethylaminocoumarin-4-yl)-methyl-GABA-trifluoroacetate (4)

(7-N,N-diethylaminocoumarin-4-yl)-methyl-N-t-BOC-GABA-ester 3 (1.0 g, 2.31 mmol) was dissolved in 150 ml of dichloromethane and the reaction mixture was cooled to 0° C. Trifluoroacetic acid (5 ml) was added slowly and resulting solution was stirred in dark for 24 h. bringing it to room temperature. The solvent was removed under reduced pressure and isolated compound was purified over Sephadex LH-20 column with water as eluent.

$^1$H NMR (300 MHz, $D_2O$) δ 7.30 (d, J=9.0 Hz, 1H), 6.68 (dd, J=9.0, 2.6 Hz, 1H), 6.5 (d, J=2.1 Hz, 1H), 5.97 (s, 1H), 5.2 (s, 2H), 3.35 (q, J=7.1 Hz, 4H), 2.95 (t, J=7.1 Hz, 2H), 2.5 (t, J=7.1 Hz, 2H), 1.85 (m, 2H), 1.0 (t, J=7.1 Hz, 6H); Anal. Calcd for $C_{20}H_{25}N_2O_6F_3$: C, 53.81; H, 5.6; N, 6.28. Found: C, 53.61; H, 5.72; N, 6.19.

Alternatively, in order to make a DECM-caged GABA that is caged through the amino group as a carbamate (see Scheme 5 infra), 100 mg (0.41 mmol) of 2 and 1,1'-carbonyl diimidazole (78.78 mg, 0.486 mmol) in 1 ml DMSO (Aldrich) were stirred at room temperature for about 3 h. GABA (50 mg, 0.486 mmol) was added to the reaction mixture, and the resulting mixture was heated to 80° C. for about 1 h. After cooling to room temperature, 50 ml of water were added and the mixture was acidified to pH 3-4 with 1 M HCl. The precipitate was extracted with 3×40 ml ethyl acetate. The organic layers were combined, washed with 3×30 ml water, dried over $Na_2SO_4$ layer. The solvent was removed under reduced pressure. The residue was crystallized by treatment with a mixture of 1 ml acetone and 1 ml ether.

$^1$H NMR (300 MHz, DMSO) δ 7.57 (t, 1H), 7.40 (d, J=9.0 Hz, 1H), 6.65 (dd, J=9.0, 2.6 Hz, 1H), 6.47 (d, J=2.1 Hz, 1H), 5.98 (s, 1H), 5.2 (s, 2H), 3.40 (q, J=7.1 Hz, 4H), 3.05 (m, 2H), 2.22 (t, J=7.1 Hz, 2H), 1.63 (m, 2H), 1.05 (t, J=7.1 Hz, 6H).

Scheme 5

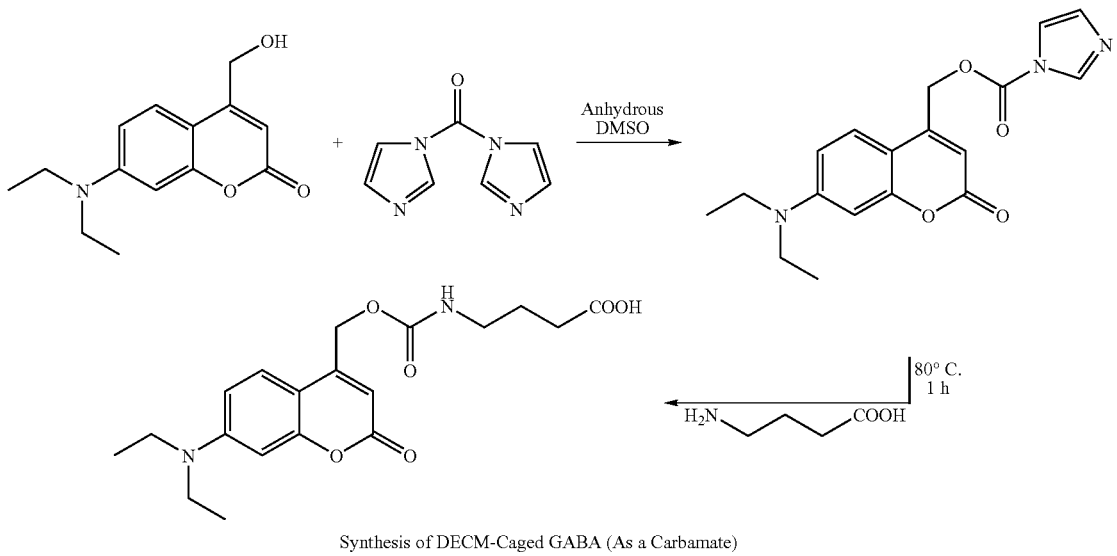

Synthesis of DECM-Caged GABA (As a Carbamate)

Example 5

Hydrolysis in the Dark

Figure 7:
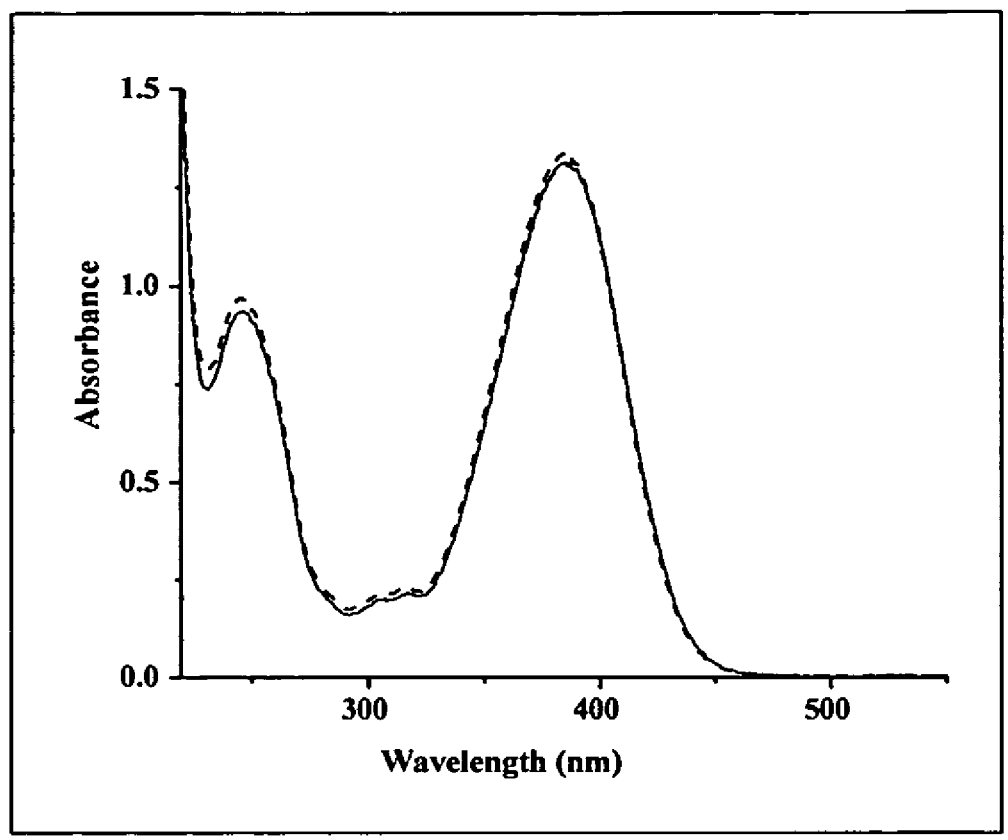
FIG. 7 illustrates the thermal hydrolysis of DECM-caged-glycine.

The caged compound (1 mM) was rapidly dissolved in the buffer solution (150 mM NaCl, 1 mM $CaCl_2$, 10 mM HEPES; the pH was adjusted to 7.4 using 5 N NaOH), and the solution was immediately transferred to a cuvette (4 mL volume, 10 mm path length) and placed in an absorption spectrometer (OLIS-14C) at 22° C. Whole spectra were recorded between 1 and 240 min after the compound was dissolved (FIGS. 1 and 7).

Example 6

Laser-Flash Photolysis (Transient Spectral Measurements)

Laser-flash photolysis experiments were done with 250 μM DECM-glutamate 4 (Scheme 1) or 250 μM DECM-glycine 4 (Scheme 2) in HEK extracellular buffer (see Example 8 for the composition), using a $XeCl_2$ excimer laser (Compex 101 Lambda Physik, Goettingen, Germany), with a single 10 ns pulse of 4.8 mJ. The energy of the beam was measured using a Molectron (Portland, Oreg.) joule meter. Light of $\geq$400 nm produced by fluorescence from $4.9 \times 10^{-4}$ M Exalite 404 dye (Exciton Inc., Dayton, Ohio) was used to initiate photolysis. The decay of the transient intermediate absorbance was recorded by digitizing the photomultiplier output at rates up to 2 MHz. The transient absorption changes were monitored at a wavelength where there was significant change in the absorption on irradiation of the caged compound (ca. 460 nm). All photolysis rates and quantum yields were measured at room temperature. Nonlinear least-squares fitting of single exponential decays was used to determine the photolysis rate constants.

Example 7

Quantum Yield

The quantum yield for the caged compound was determined by actinometric methods (Murov, in Dekker, ed., *Handbook of Photochemistry*, New York, pp. 298-305 (1993), which is hereby incorporated by reference in its entirety). The Oriel (Oriel Instruments, Stratford, Conn.) lamp used for photolysis was equipped with a filter (Schott glass filter GG400; Schott North America, Inc., Elmsford, N.Y.) to eliminate light at wavelengths below 400 nm.

The quantum yield was also determined using the method published by Milburn et al., "Synthesis, Photochemistry, and Biological Activity of a Caged Photolabile Acetylcholine Receptor Ligand," *Biochemistry* 28:49-55 (1989), which is hereby incorporated by reference in its entirety. For measuring the quantum yield of DECM-caged glutamate photolysis, 3 mL sample of 4 (Scheme 1) was photolyzed with repetitive light pulses at $\geq$400 nm, and the concentration of 2 (Scheme 1) was determined spectrophotometrically. For measuring the quantum yield of DECM-caged glycine photolysis, 3 mL sample of 4 (Scheme 2) was photolyzed with repetitive light pulses at $\geq$400 nm, and the concentration of 2 (Scheme 2) was determined spectrophotometrically.

Example 8

Whole-Cell Current Recording

In whole-cell current recording experiments with DECM-caged glutamate, HEK 293 cells stably transfected with cDNA encoding the GluR6 were used. In whole-cell current recording experiments with DECM-caged glycine, HEK 293 cells were transiently transfected with the cDNA of the α1-subunit of the human glycine receptor by using the Polyfect™ transfection reagent (Qiagen GmbH, D-40724, Hilden, Germany). The cDNA of the α1-subunit was kindly provided by Professor H. Betz (Max-Plank-Institute for brain Research, Frankfurt, Germany). The cells were co-transfected with cDNA encoding the green fluorescent protein (pGreen Lantern plasmid, Life Technologies, Gaitherberg, Md.) to detect transfected cells (Chalfie et al., "Green Fluorescent Protein as a Marker for Gene Expression," *Science* 263:802-805 (1994), which is hereby incorporated by reference in its entirety).

Figure 5:
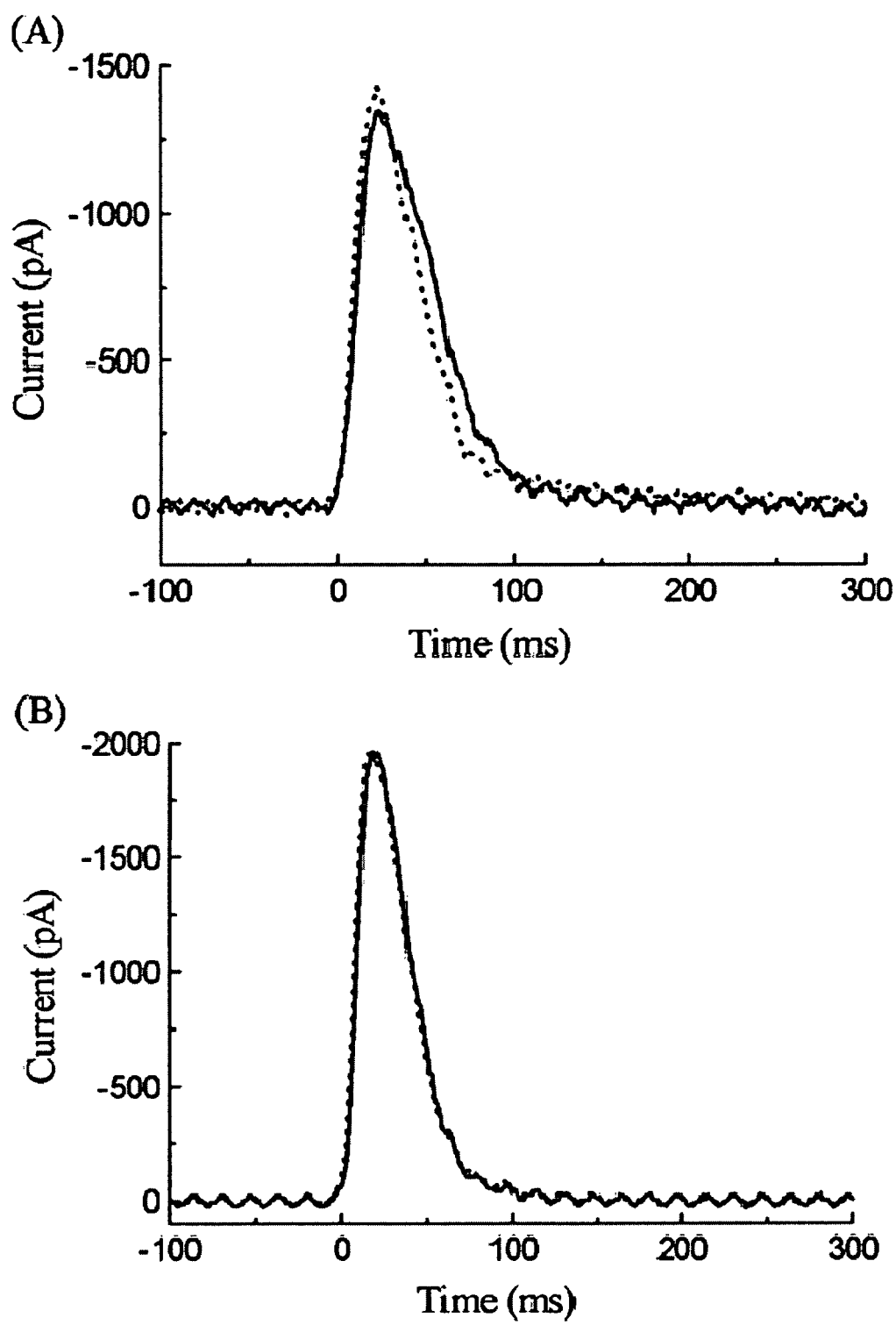
FIGS. 5A-B illustrate that the DECM-caged glutamate and 7-N,N-diethylamino-4-hydroxymethylcoumarin, DECM (compound 2 in Scheme 1), do not inhibit the current evoked by glutamic acid. 100 μM glutamate, using the cell-flow technique (Udgaonkar et al., "Chemical Kinetic Measurements of a Mammalian Acetylcholine Receptor by a Fast-Reaction Technique," *Proc Natl Acad Sci USA* 84:8758-8762 (1987); Krishtal et al., "A Receptor for Protons in the Nerve Cell Membrane," *Neuroscience* 5:2325-2327 (1980), which are hereby incorporated by reference in their entirety), was allowed to flow over the surface of an HEK 293 cell transfected with cDNA encoding the GluR6 glutamate receptor (V=−60 mV, HEK buffer, pH 7.4, 22° C.) (FIG. 5A) in the absence (solid line) or presence (dotted line) of 2 mM DECM-caged glutamate, and (FIG. 5B) in the absence (solid line) or presence (dotted line) of 1 mM DECM. The induced current was recorded in the whole-cell configuration. Using the cell-flow technique for application of the ligand (Udgaonkar et al., "Chemical Kinetic Measurements of a Mammalian Acetylcholine Receptor by a Fast-Reaction Technique," *Proc Natl Acad Sci USA* 84:8758-8762 (1987), which is hereby incorporated by reference in its entirety), experiments were carried out at least three times on at least two different cells.
Figure 10:
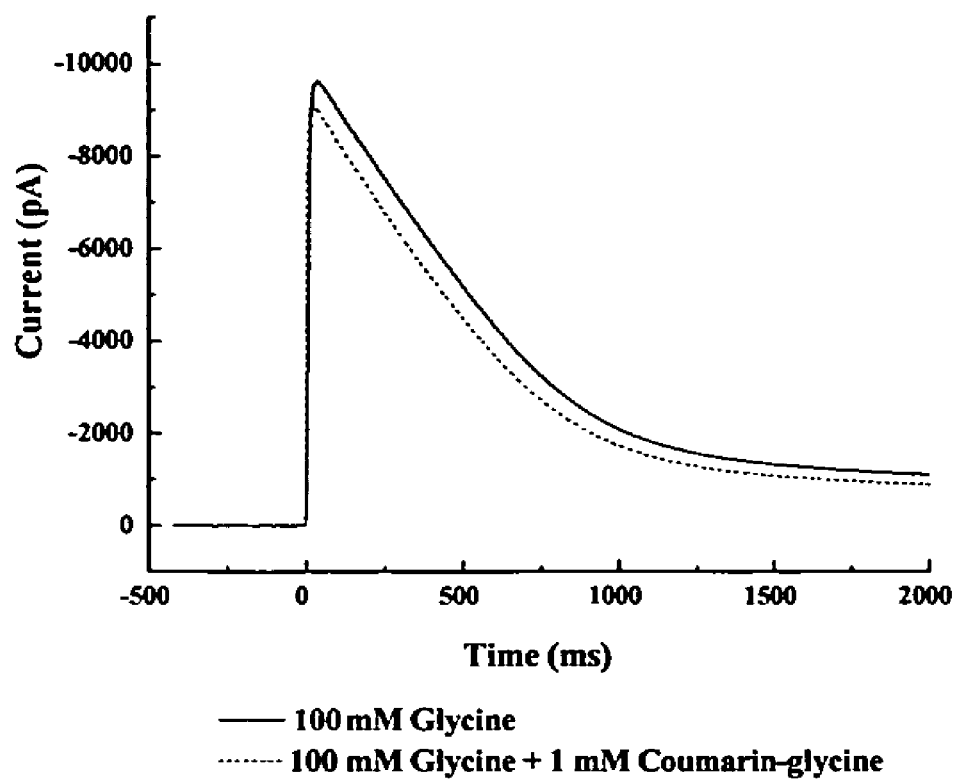
FIG. 10 shows that DECM-caged glycine does not inhibit the current evoked by glycine. Using the cell-flow technique (Udgaonkar et al., "Chemical Kinetic Measurements of a Mammalian Acetylcholine Receptor by a Fast-Reaction Technique," *Proc Natl Acad Sci USA* 84:8758-8762 (1987); Krishtal et al., "A Receptor for Protons in the Nerve Cell Membrane," *Neuroscience* 5:2325-2327 (1980), which are hereby incorporated by reference in their entirety), 100 µM glycine was allowed to flow over the surface of an HEK 293 cell transfected with cDNA encoding the glycine receptor (transmembrane voltage −60 mV, HEK extracellular buffer, pH 7.4, 22° C.) in the absence (solid line) or presence (dotted line) of 2 mM DECM-caged glycine. The induced current was recorded in the whole-cell configuration. Using the cell-flow technique for application of the ligand (Udgaonkar et al., "Chemical Kinetic Measurements of a Mammalian Acetylcholine Receptor by a Fast-Reaction Technique," *Proc Natl Acad Sci USA* 84:8758-8762 (1987), which is hereby incorporated by reference in its entirety), experiments were carried out at least three times on at least two different cells.

The cells were used for electrophysiological experiments between 24 and 72 h after each passage. Whole-cell currents evoked by glutamate or glycine (100 μM) were recorded using the whole-cell configuration (Hamill et al., "Improved Patch-Clamp Techniques for High-Resolution Current Recording From Cells and Cell-Free Membrane Patches," *Pfluegers Arch* 391:85-100 (1981), which is hereby incorporated by reference in its entirety) at room temperature, −60 mV, and pH 7.4. The experiments using DECM-caged glutamate were carried out in the absence or presence of 2 mM DECM-caged glutamate (FIG. 5A) or 1 mM 7-N,N-diethylamino-4-hydroxymethylcoumarin (2) (FIG. 5B). Alternatively, the experiments using DECM-caged glycine were carried out in the absence or presence of 1 mM DECM-caged-glycine (FIG. 10). The solution in the recording pipet contained 120 mM CsCl, 10 mM EGTA, and 10 mM HEPES, adjusted to pH 7.4. The HEK cell bath solution contained 150 mM NaCl, 1 mM $CaCl_2$, 10 mM HEPES, pH 7.4. The resistance of the recording electrode filled with buffer solution was typically 3-5 MΩ and the series resistance was 5-6 MΩ. The cells were held at a constant transmembrane voltage of −60 mV and room temperature (22° C.). Whole-cell currents were amplified by using an Axopatch 200B (Axon Instruments, Foster City, Calif.) amplifier and filtered at 1-5 kHz by using a 40-pole, low-pass, Bessel (Dagan Corporation, Minneapolis, Minn.) filter incorporated in the amplifier. The filtered signal was digitized by a Digidata 1322A (Axon Instruments, Union City, Calif.) or a Labmaster DMA 100 KHz digitizing board (Scientific Solutions, Mentor, Ohio) controlled by pCLAMP9 software (Axon Instruments).

Example 9

Cell-Flow Method

The use of a U-tube flow device for rapid solution exchange at the surface of a cell has been described in detail (Udgaonkar et al., "Chemical Kinetic Measurements of a Mammalian Acetylcholine Receptor by a Fast-Reaction Technique," *Proc Natl Acad Sci USA* 84:8758-8762 (1987); Krishtal et al., "A Receptor for Protons in the Nerve Cell Membrane," *Neuroscience* 5:2325-2327 (1980); Niu et al., "Chemical Kinetic Investigations of Neurotransmitter Receptors on a Cell Surface in the μs Time Region," *Tech Protein Chem VII* 139-149 (1996), which are hereby incorporated by reference in their entirety). The device, consisting of a U-tube and a preincubation tube, allows one to preincubate a solution of a compound with a cell before a solution containing this and/or other compounds, such as the receptor activating ligand, are allowed to flow over the cell (Niu et al., "Chemical Kinetic Investigations of Neurotransmitter Receptors on a Cell Surface in the μs Time Region," *Tech Protein Chem VII* 139-149 (1996), which is hereby incorporated by reference in its entirety). The maximum amplitude of the current is a measure of the concentration of open receptor-channels. In cell-flow experiments, the observed maximum current amplitude was corrected for the desensitization that occurs while the receptors equilibrate with the channel-activating ligand in the solution flowing over the cell surface (Udgaonkar et al., "Chemical Kinetic Measurements of a Mammalian Acetylcholine Receptor by a Fast-Reaction Technique," *Proc Natl Acad Sci USA* 84:8758-8762 (1987); Hess et al., "Chemical Kinetic Measurements of Transmembrane Processes Using Rapid Reaction Techniques: Acetylcholine Receptor," *Annu Rev Biophys Chem* 16:507-534 (1987), which are hereby incorporated by reference in their entirety). This provides the maximum current amplitude corrected for the desensitization.

Example 10

Laser-Pulse Photolysis of DECM-Caged Glutamate

The laser light produced by the Exalite (Exiton Inc., Dayton, Ohio) 404 dye (≅400 nm) was coupled into an optical fiber (300 μm internal diameter), which delivered the light to the cell. The concentration of DECM-caged glutamate used was 2 mM for the results in FIG. 6. Typical laser energies were 150-250 μJ per pulse. The amount of glutamate liberated was calibrated by cell-flow experiments before and after the laser pulse with a standard glutamate solution (100 μM) and the known dose-response curve for glutamate (Li et al., "Channel-Opening Kinetics of GluR6 Kainate Receptor," *Biochemistry* 42:12367-12375 (2003), which is hereby incorporated by reference in its entirety). The pulse/flow system was computer-controlled with pClamp9 software (Axon instruments). Data were sampled at 5-100 kHz and low-pass filtered at 2-10 kHz. Data were analyzed with Microcal Origin3.5 software (Microcal, Northampton, Mass.).

Example 11

Flash Lamp Photolysis of DECM-Caged Glycine

The light produced by the Rapp (Rapp OptoElectronics, Hamburg, Germany) xenon flash lamp (SP-20) was coupled into an optical fiber (600 μm internal diameter), which delivered the light to the cell. The concentration of DECM-caged-glycine used was 1 mM for the results in FIG. 11. Typical light energies were 150-250 μJ per pulse. The amount of glycine liberated was calibrated by cell-flow experiments before and after the light pulse with a standard glycine solution (100 μM) and the known dose-response curve for glycine (Grewer, C., "Investigation of the Alpha(1)-glycine Receptor Channel-Opening Kinetics in the Submillisecond Time Domain," *Biophys J* 77(2):727-738 (1999), which is hereby incorporated by reference in its entirety). The pulse/flow system was computer-controlled with pClamp6 software (Axon instruments). Data were sampled at 5-100 kHz and low-pass filtered at 2-10 kHz. Data were analyzed with Microcal Origin3.5 software (Microcal, Northampton, Mass.).

Example 12

Results of DECM-Caged Glutamate Photolysis

Synthesis of 7-N,N-diethylamino 4-hydroxymethyl coumarin caged glutamic acid (compound 4) is shown in Scheme 1 and described above in detail in Example 1.

The absorption spectrum and the thermal stability of the caged compound 4 (Scheme 1) were measured in HEK buffer solution at pH 7.4. The caged compound protected from light showed very little hydrolysis at room temperature during 2 h of measurements (FIG. 1). No measurable hydrolysis was observed during 24 h when the caged glutamate dissolved in buffer, pH 7.4, was stored at −20° C. in the dark.

The stability of DECM-caged glutamate in aqueous solution was also tested using HEK 293 cells transfected with cDNA encoding the GluR6 glutamate receptor as a highly sensitive glutamate detector (Wieboldt et al., "Photolabile Precursors of Glutamate: Synthesis, Photochemical Properties, and Activation of Glutamate Receptors on a Microsecond Time Scale," *Proc Natl Acad Sci USA* 91:8752-8756 (1994), which is hereby incorporated by reference in its entirety). The concentration of free glutamate in a 2 mM solution of DECM-caged glutamate was measured as a function of time after solubilization at pH 7.4 at room temperature, by whole-cell recording. After 24 h in the dark at −20° C. and pH 7.4, no free glutamate was detected in this experiment.

Figure 2:
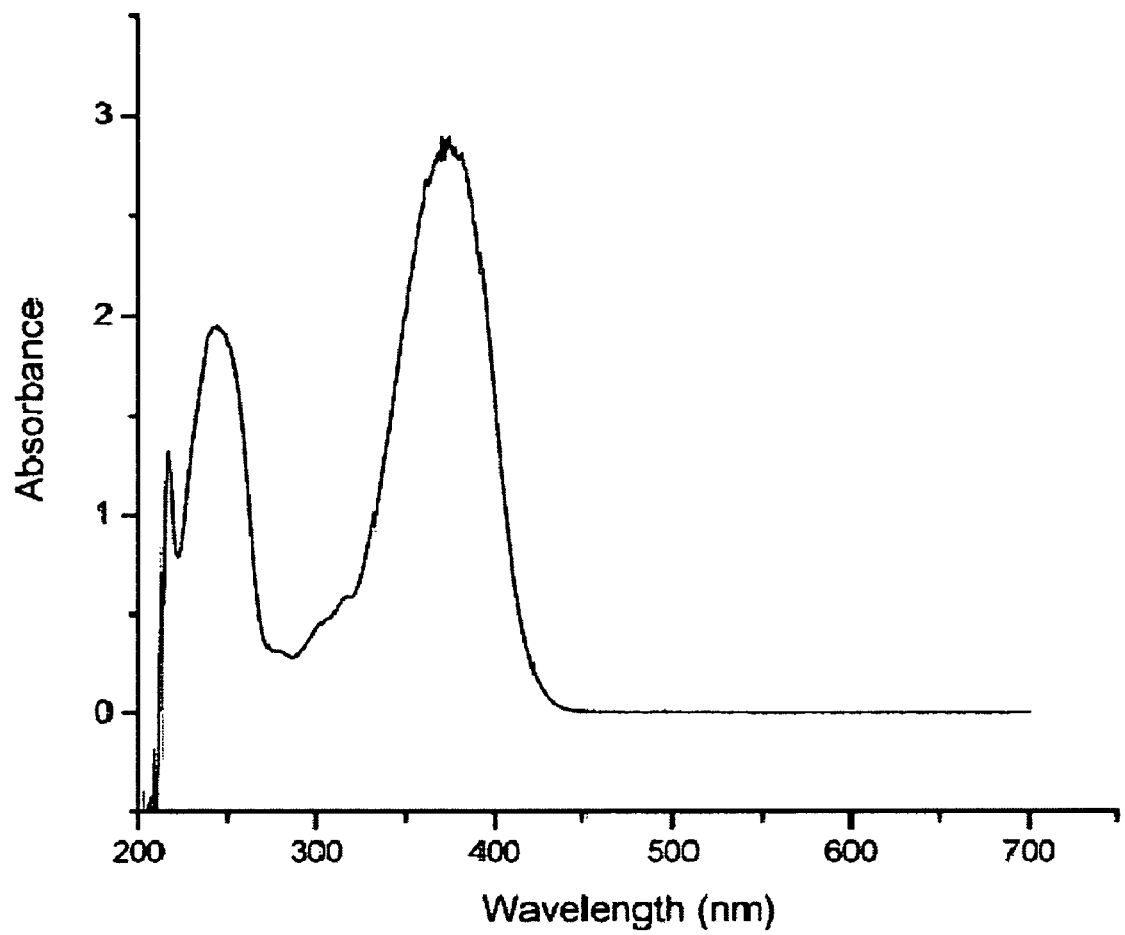
FIG. 2 shows a UV-visible absorption spectrum of compound 2 (Scheme 1), 7-N,N-diethylamino-4-hydroxymethylcoumarin, which is the DECM photolysis byproduct.
Figure 3:
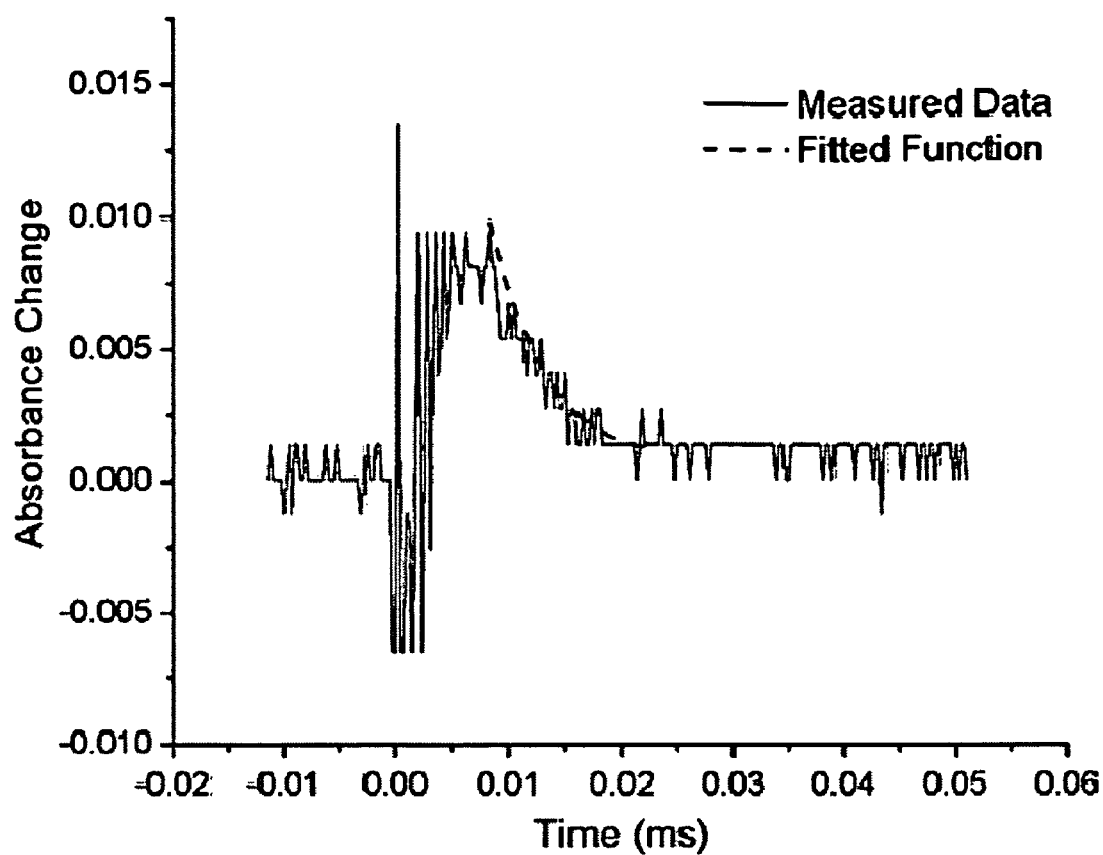
FIG. 3 illustrates the absorption transient at 460 nm observed in the photolysis of DECM-caged glutamic acid (compound 4 in Scheme 1), produced by a light pulse at ≧400 nm in a 0.8 mM solution of compound 4 in 100 mM extracellular HEK buffer, pH 7.4 and 22° C. The single-exponential absorbance decay has a time constant of 3 μs. The solid line represents the measured data and the dotted line the fitted curve. The absorbance change observed at zero time is produced by discharge of the laser power supply and is also observed in the absence of caged glutamate.

The rate constant of glutamate release was estimated by measuring the rate constant for formation of 7-N,N-diethylamino-4-hydroxymethylcoumarin 2 (Scheme 1) (FIG. 2). Formation of 2 is indirect evidence of release of free neurotransmitter. After a solution of caged glutamate was excited with a pulse of 10 ns, of ≧400 nm light, the absorbance of 2, one of the products, was measured as a function of time, at 460 nm (FIG. 3). The transient absorbance decayed with a single-exponential component and a $t_{1/2}$ of 3 µs. Therefore, it appeared that the caged compound was suitable for kinetic measurements of fast cellular processes in the microsecond time domain.

Figure 4:
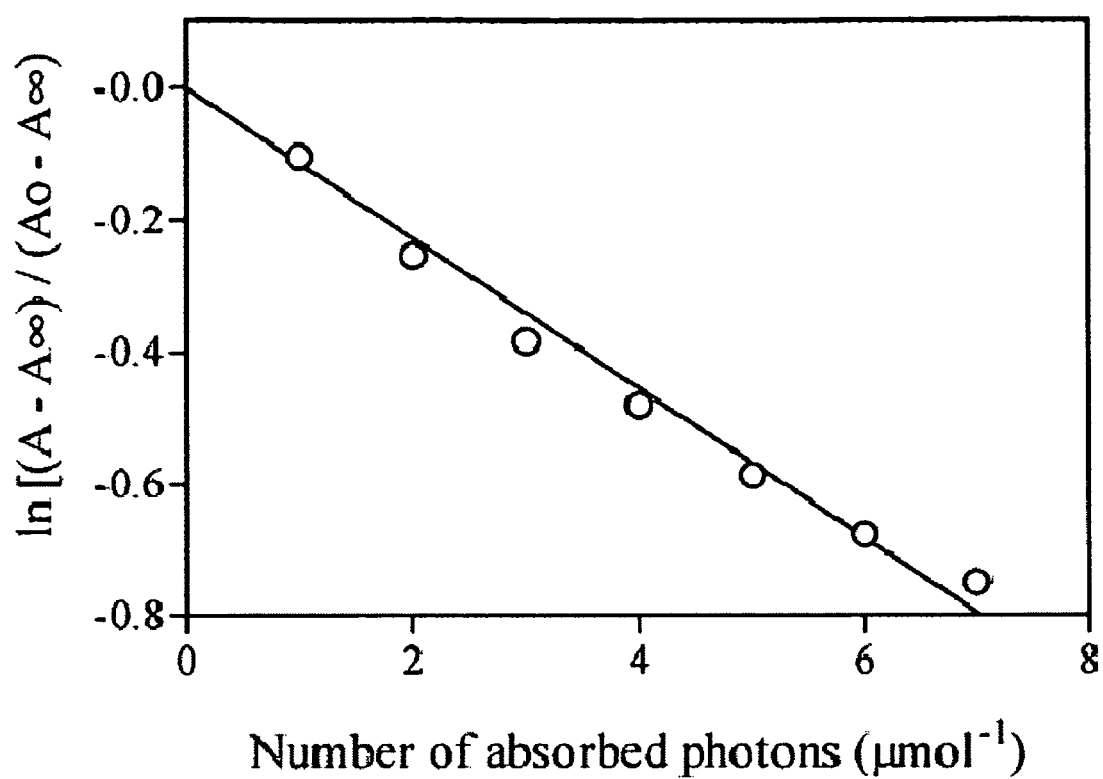
FIG. 4 shows absorbance (A) of a 250 μM DECM-caged glutamate solution in extracellular buffer at pH 7.4 and 22° C. measured as a function of the number of laser flashes at the excitation wavelength of 400 nm. The solution (3 mL) was irradiated in a 10×10 mm cuvette. The solution was stirred after every 20th laser flash. The line corresponds to the results of a linear regression representing the slope of 0.11±0.08, which gives the quantum yield of the photolysis of the caged glutamate. The data were fitted to equation 1 (see Example 12).

For a photolabile caging group to be useful for biological applications, the quantum yield of the photochemical step should be high (criterion 3; see Background of the Invention section) so that the neurotransmitter is released in sufficient quantity at the desired site at a light intensity that is not harmful to the cell. The quantum yield of DECM-caged glutamate was determined at ≧400 nm as described in Milburn et al., "Synthesis, Photochemistry, and Biological Activity of a Caged Photolabile Acetylcholine Receptor Ligand," *Biochemistry* 28:49-55 (1989), which is hereby incorporated by reference in its entirety. FIG. 4 shows the change in the absorbance of the caged compound as a function of the number of photons absorbed from the light pulses at ≧400 nm (Milburn et al., "Synthesis, Photochemistry, and Biological Activity of a Caged Photolabile Acetylcholine Receptor Ligand," *Biochemistry* 28:49-55 (1989), which is hereby incorporated by reference in its entirety). The absorbance A measured as a function of the number of consecutive light pulses was plotted in a semilogarithmic fashion (FIG. 4) according to equation I (Milburn et al., "Synthesis, Photochemistry, and Biological Activity of a Caged Photolabile Acetylcholine Receptor Ligand," *Biochemistry* 28:49-55 (1989), which is hereby incorporated by reference in its entirety).

$$An = \epsilon_m l C_0 \phi K_E \exp[-\phi K_E F(n-1)] \qquad (I)$$

An represents the absorbance after the nth pulse, $\epsilon_m$ the extinction coefficient of the product, l the path length, $C_0$ the initial concentration of the caged compound, $\phi$ the quantum yield, $K_E$ the ratio of the absorbed photons to the number of target molecules (constant), and F the fraction of solution containing the caged compound through which the laser beam passes. The quantum yield was determined from the slope of the plot in FIG. 4 and was calculated by linear regression analysis to be 0.11±0.008 (FIG. 4).

To be useful in investigations of neurotransmitter receptors, the caged compound and the photolysis byproducts must not inhibit or activate the receptors to be investigated. The HEK 293 cells transfected with cDNA encoding the GluR6 glutamate receptor were exposed to 100 µM glutamate in the presence and absence of 2 mM DECM-caged glutamate (compound 4 in Scheme 1) (FIG. 5A) or in the presence or absence of 1 mM of the photolysis byproduct, 7-N,N-diethylamino-4-hydroxymethylcoumarin (compound 2 in Scheme 1) (FIG. 5B) at pH 7.4 at 22° C. The whole-cell currents recorded in the presence and absence of DECM-caged glutamate (FIG. 5A) or the photolysis byproduct (FIG. 5B) at concentrations as high as 2 mM were the same. These control experiments indicate that in this system the DECM-caged glutamate and its photolysis byproducts are biologically inert.

Figure 6:
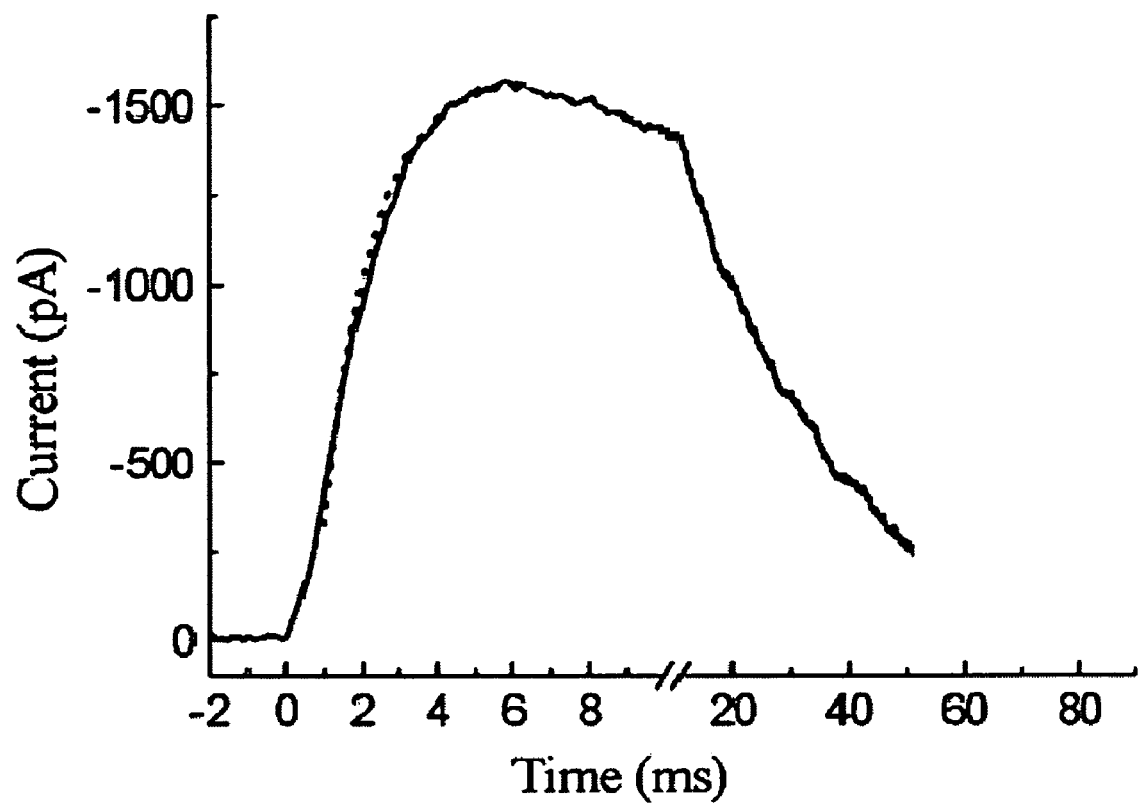
FIG. 6 depicts the whole-cell current recorded from an HEK 293 cell transfected with cDNA encoding the GluR6 glutamate receptor, at V=−60 mV, HEK buffer, pH 7.4, and 22° C. The current was induced by the photolytic release of glutamate from 2 mM DECM-caged glutamate, which was equilibrated with the receptors for 400 ms before exposing it to a laser pulse of visible light, delivering 240 μJ of energy. The concentration of liberated glutamate was estimated to be ~300 μM (see Example 12). The dotted line represents the best fit according to the equation $I_{(t)}=I_\infty[1-\exp(-k_{obs}t)]$ (Hess et al., "Development and Application of Caged Ligands for Neurotransmitter Receptors in Transient Kinetic and Neuronal Circuit Mapping Studies," *Methods in Enzymology. Caged Compounds* 291:443-473 (1998), which is hereby incorporated by reference in its entirety) with $k_{obs}$=765±14 s$^{-1}$ and $I_\infty$=−1590 pA. $I_{(t)}$ is the current at time t, $I_\infty$ is the current at t=∞ (in the absence of desensitization), and $k_{obs}$ is the apparent pseudo-first-order rate constant of the current rise.

The laser-pulse photolysis at ≧400 nm of 2 mM caged compound was carried out with HEK 293 cells transfected with cDNA encoding the GluR6 glutamate receptor. The whole-cell current induced by the released glutamate was recorded as a function of time (FIG. 6). A standard solution (100 µM) of glutamate flowed over the cell and the whole-cell current was recorded before and after the laser-pulse photolysis measurement to determine that neither the cell membrane nor the receptors were damaged. These experiments were also used to estimate the concentration of glutamate released from the caged compound (FIG. 6). Laser-pulse photolysis of 2 mM DECM-caged glutamate at 400 nm induced currents, indicated the release of 300 µM glutamate as estimated from control cell-flow experiments (Udgaonkar et al., "Chemical Kinetic Measurements of a Mammalian Acetylcholine Receptor by a Fast-Reaction Technique," *Proc Natl Acad Sci USA* 84:8758-8762 (1987), which is hereby incorporated by reference in its entirety) with a standard concentration of glutamate.

Example 13

Results of DECM-Caged Glycine Photolysis

The synthesis of 7-N,N-diethylamino 4-hydroxymethyl coumarin caged glycine (compound 4) is shown in Scheme 2, and described above in detail in Example 2.

The absorption spectrum and the thermal stability of the caged compound 4 (Scheme 2) were measured in HEK buffer solution at pH 7.4. When protected from light, the caged compound showed very little hydrolysis at room temperature during two hours of measurements (FIG. 7). No measurable hydrolysis was observed during 20 h when the caged glycine dissolved in buffer, pH 7.4, was stored at −20° C. in the dark.

The stability of DECM-caged glycine in aqueous solution was also tested using HEK 293 cells transfected with cDNA encoding the α1-subunit human glycine receptor as a highly sensitive glycine detector (Wieboldt et al., "Photolabile Precursors of Glutamate: Synthesis, Photochemical Properties, and Activation of Glutamate Receptors on a Microsecond Time Scale," *Proc Natl Acad Sci USA* 91:8752-8756 (1994), which is hereby incorporated by reference in its entirety). The concentration of free glycine in a 1 mM solution of DECM-caged glycine, liberated as a result of hydrolysis, was measured as a function of time after solubilization at pH 7.4 and room temperature, by whole-cell current recording. After 20 hours in the dark at −80° C. and pH 7.4, no free glycine was detected in this experiment.

Figure 8:
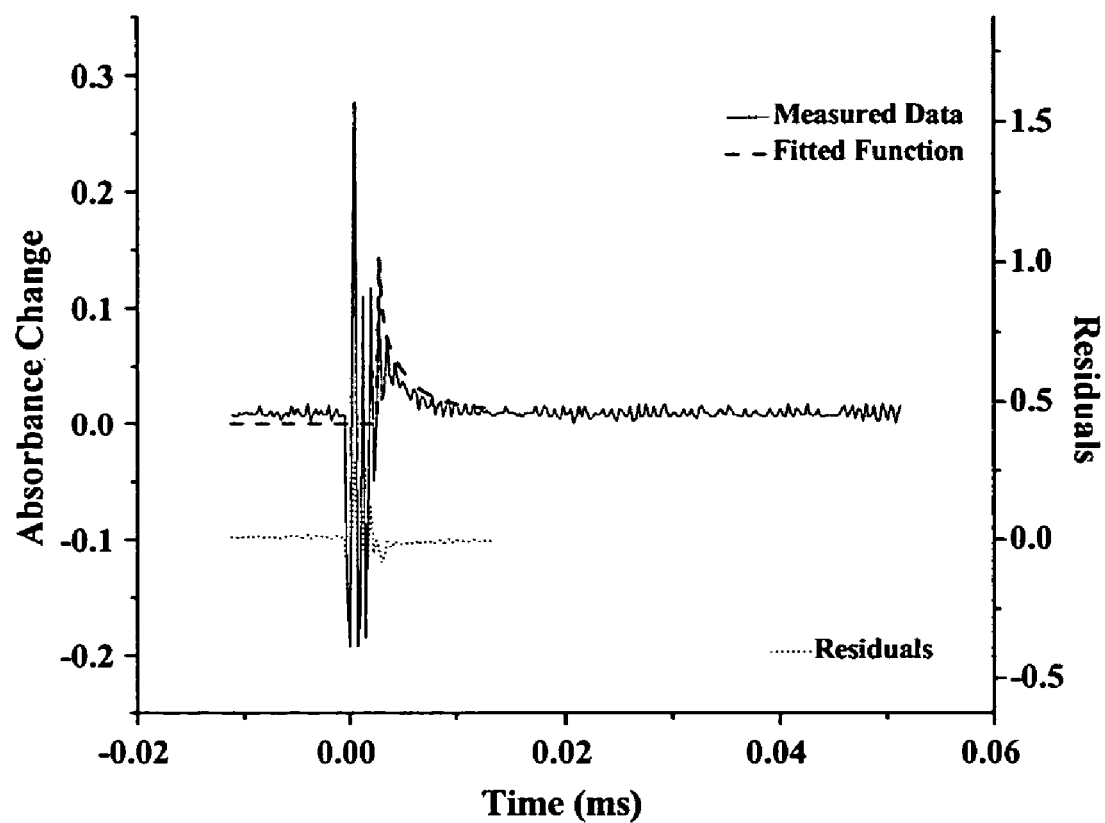
FIG. 8 shows the absorption transient at 460 nm observed in the photolysis of DECM-caged glycine (compound 4 in Scheme 2), produced by a light pulse at ≧400 nm in an 0.8 mM solution of compound 4 in 100 mM extracellular HEK buffer, pH 7.4 and 22° C. The single-exponential absorbance decay has a time constant of 2.6 μs. The solid line represents the measured data and the dotted line the fitted curve. The absorbance change observed at zero time is produced by discharge of the laser power supply and is also observed in the absence of caged glutamate.

Formation of 7-N,N-diethylamino-4-hydroxymethylcoumarin, 2 (Scheme 2), is indirect evidence of release of free neurotransmitter. The rate constant of glycine release was estimated by measuring the rate constant for formation of 2. A solution of caged glycine was excited with a 10-ns pulse of ≧400 nm light. The absorbance of 2, one of the products, was measured at 460 nm as a function of time (FIG. 8). The transient absorbance decayed with a single exponential component and a $t_{1/2}$ of 2.6 µs. Therefore, DECM-caged glycine appeared to be suitable for kinetic measurements of the glycine receptor in the microsecond time domain.

Figure 9:
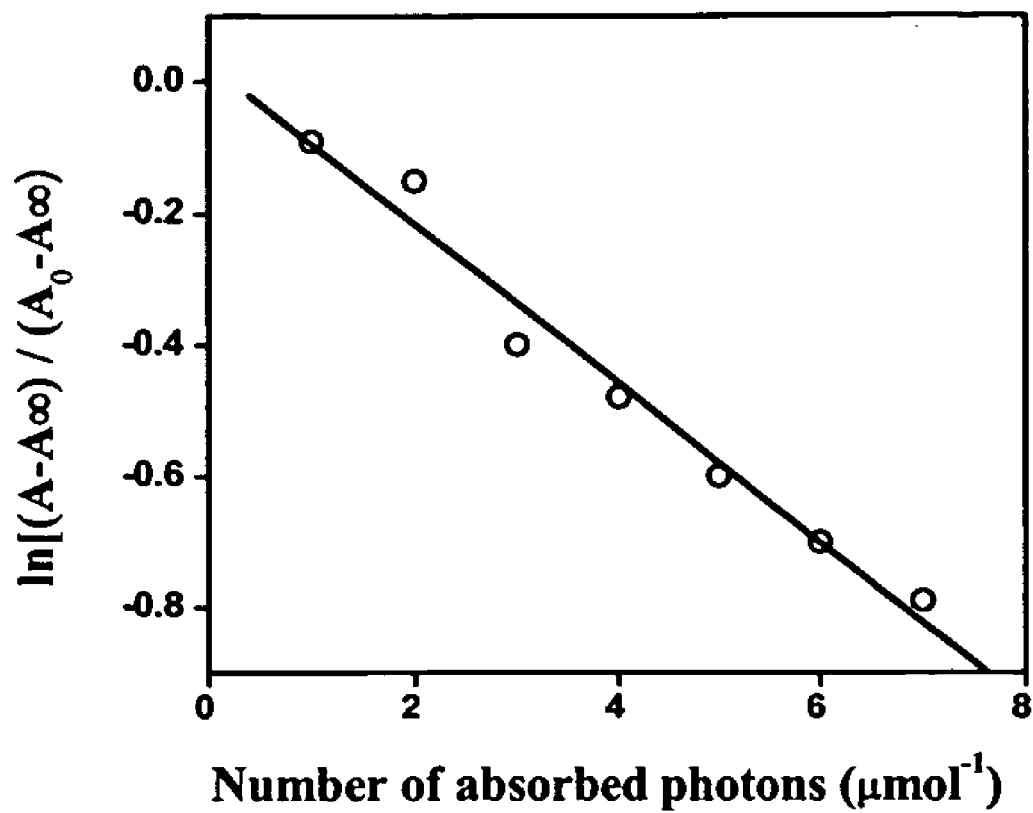
FIG. 9 depicts the absorbance (A) of a 250 µM DECM-caged glycine solution in HEK293 extracellular buffer at pH 7.4 and 22° C. measured as a function of the number of laser flashes at the excitation wavelength of 400 nm. The solution (3 mL) was irradiated in a 10×10 mm cuvette. The solution was stirred after every 20th laser flash. The line corresponds to the results of a linear regression representing the slope of 0.12±0.009, which gives the quantum yield of the photolysis of the caged glycine. The data were fitted to equation I (see Example 12).

One of the important criteria for a photolabile caging group to be useful for biological applications is that the efficiency of photolytic release of the biomolecule should be high so that a substantial concentration of the biomolecule is released at the desired site at a light intensity that is not harmful to the cell. The quantum yield of DECM-caged glycine was determined at≧400 nm, as described in Milbum et al., "Synthesis, Photochemistry, and Biological Activity of a Caged Photolabile Acetylcholine Receptor Ligand," *Biochemistry* 28:49-55 (1989), which is hereby incorporated by reference in its entirety. The change in the absorbance of the caged compound as a function of the number of photons absorbed from the light pulses at≧400 nm (Milbum et al., "Synthesis, Photochemistry, and Biological Activity of a Caged Photolabile Acetylcholine Receptor Ligand," *Biochemistry* 28:49-55 (1989); which is hereby incorporated by reference in its entirety) is shown in FIG. 9. The absorbance A measured as a function of the number of consecutive light pulses was plotted in a semilogarithmic fashion (FIG. 10) according to equation I shown above in Example 11 (Milbum et al., "Synthesis, Photochemistry, and Biological Activity of a Caged Photolabile Acetylcholine Receptor Ligand," *Biochemistry* 28:49-55 (1989), which is hereby incorporated by reference in its entirety). The quantum yield was determined from the slope of the plot in FIG. 10 and was calculated by linear regression analysis to be 0.12±0.009 (FIG. 9).

To be useful in investigations of neurotransmitter receptors, the caged compound and the photolysis byproducts must not inhibit or activate the receptors to be investigated. The HEK 293 cells transfected with cDNA encoding the glycine receptor were exposed to 100 µM glycine in the presence and absence of 1 mM DECM-caged glycine (compound 4 in Scheme 2) (FIG. 10) at pH 7.4 and 22° C. The whole-cell currents recorded in the presence and absence of DECM-caged glycine (FIG. 10) at concentrations as high as 1 mM were the same. These control experiments indicate that in this system the DECM-caged glycine and its photolysis byproducts are biologically inert.

Figure 11:
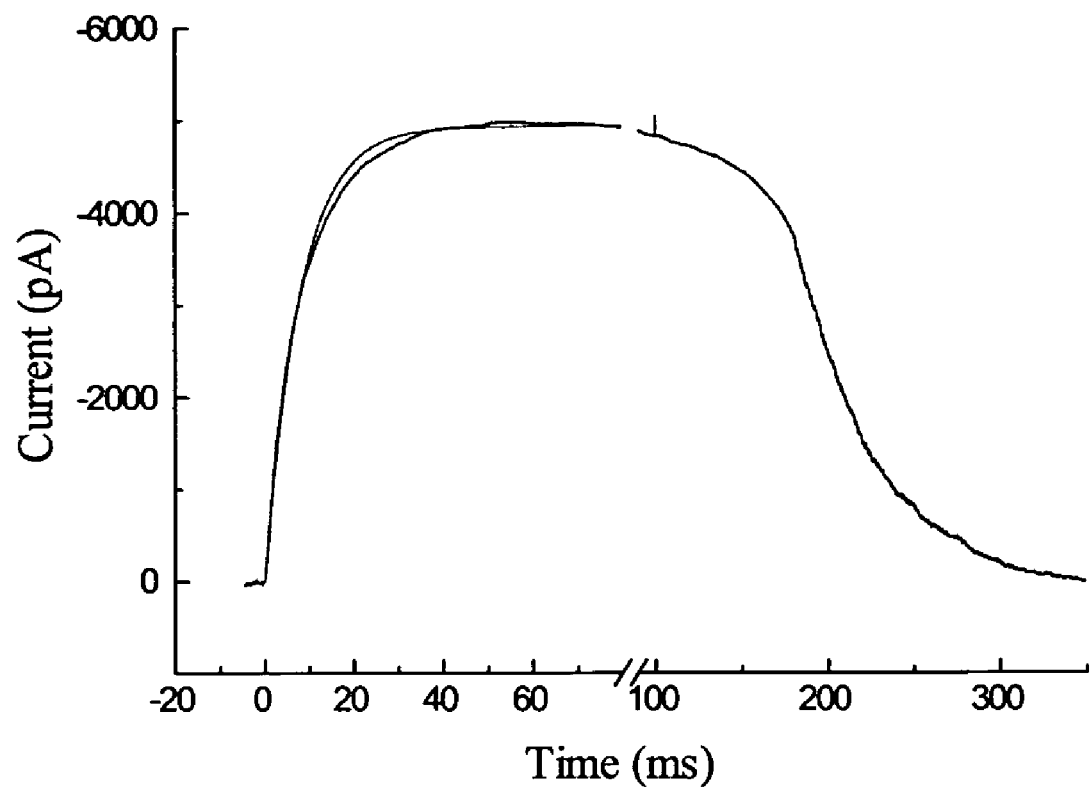
FIG. 11 depicts the whole-cell current recorded from an HEK 293 cell transfected with cDNA encoding the glycine receptor, at a transmembrane voltage of −60 mV, HEK extracellular buffer, pH 7.4, and 22° C. The current was induced by the photolytic release of glutamate from 1 mM DECM-caged glycine, which was equilibrated with the receptors for 400 ms before exposing it to a laser pulse of visible light, delivering 250 µJ of energy. The concentration of liberated glycine was estimated to be ~60 µM (see Example 13). The dotted line represents the best fit according to the equation $I_{(t)}=I_\infty[1-\exp(-k_{obs}t)]$ (Hess et al., "Development and Application of Caged Ligands for Neurotransmitter Receptors in Transient Kinetic and Neuronal Circuit Mapping Studies," *Methods in Enzymology. Caged Compounds* 291:443-473 (1998), which is hereby incorporated by reference in its entirety) with $k_{obs}=125\pm16$ s$^{-1}$ and $I_\infty=-4950\pm57$ pA. $I_{(t)}$ is the current at time t, $I_\infty$ the current at t=∞ (in the absence of desensitization), and $k_{obs}$ is the apparent pseudo first-order rate constant of the current rise.

The flash-lamp photolysis at≧385 nm of 1 mM caged compound was carried out with HEK 293 cells transfected with cDNA encoding the glycine receptor. The whole-cell current induced by the released glycine was recorded as a function of time (FIG. 11). A standard solution (100 µM) of glycine flowed over the cell and the whole-cell current was recorded before and after the laser-pulse photolysis measurement to determine that neither the cell membrane nor the receptors were damaged. These experiments were also used to estimate the concentration of glycine released from the caged compound (FIG. 11). Flash-lamp photolysis of 1 mM DECM-caged glycine at 400 nm induced currents that indicated the release of 60 µM glycine as estimated from control cell-flow experiments (Udgaonkar et al., "Chemical Kinetic Measurements of a Mammalian Acetylcholine Receptor by a Fast-Reaction Technique," *Proc Natl Acad Sci USA* 84:8758-8762 (1987), which is hereby incorporated by reference in its entirety) with a standard concentration (100 µM) of glycine.

Example 14

A Protecting Group for Carboxylic Acids that can be Photolyzed by Visible Light

Photolabile DECM-caged glutamate and DECM-caged glycine were synthesized from readily available starting materials. Care had to be taken to protect the DECM-caged glutamate from light, particularly when aqueous solutions were handled. The caged compound was sufficiently soluble in water or the buffers used and was stable in the dark. Upon irradiation with a pulse of light, glutamate was released from the caged precursor in the visible wavelength region rapidly ($t_{1/2}$~3 µs) and with sufficient quantum yield to be used in transient chemical kinetic investigations (Hess G., "Rapid Chemical Reaction Techniques Developed for Use in Investigations of Membrane-Bound Proteins (Neurotransmitter Receptors)," *Biophys Chem* 100:493-506 (2003); Hess et al., "Development and Application of Caged Ligands for Neurotransmitter Receptors in Transient Kinetic and Neuronal Circuit Mapping Studies," *Methods Enzymol: Caged Compd* 291:443-473 (1998), which are hereby incorporated by reference in their entirety). In addition, upon irradiation with a pulse of light, glycine was released from the caged precursor in the visible wavelength region rapidly ($t_{1/2}$~2.6 µs) and with sufficient quantum yield to be used in transient chemical kinetic investigations (Hess G., "Rapid Chemical Reaction Techniques Developed for Use in Investigations of Membrane-Bound Proteins (Neurotransmitter Receptors)," *Biophys Chem* 100:493-506 (2003); Hess et al., "Development and Application of Caged Ligands for Neurotransmitter Receptors in Transient Kinetic and Neuronal Circuit Mapping Studies," *Methods Enzymol: Caged Compd* 291:443-473 (1998), which are hereby incorporated by reference in their entirety). One can assume that all the other carboxyl-group-containing neurotransmitters can also be caged with DECM and will all have similar favorable properties. This indicates that in transient kinetic investigations of these receptors in which the caged neurotransmitters were photolyzed in the UV region in previous experiments (Hess G., "Rapid Chemical Reaction Techniques Developed for Use in Investigations of Membrane-Bound Proteins (Neurotransmitter Receptors)," *Biophys Chem* 100:493-506 (2003); Gee et al., "Synthesis, Photochemistry, and Biological Characterization of Photolabile Protecting Groups for Carboxylic Acids and Neurotransmitters," *Methods Enzymol: Caged Compd* 291:30-50 (1998), which are hereby incorporated by reference in their entirety), a relatively inexpensive, hazard-free and simple-to-use light sources can now be used.

Signal transmission at chemical synapses in the central nervous system utilizes neurotransmitter-gated ion-channel receptor proteins (Kandel et al., *Principles of Neuronal Science*, 2$^{nd}$ Ed. Elsevier (2000), which is hereby incorporated by reference in its entirety). These receptors open transmembrane channels selective for small inorganic cations or anions after the binding of neurotransmitter that is secreted from presynaptic cell. It is the ionic current flowing through the receptor-channels that generates a change in the membrane potential of the postsynaptic cell, thus triggering signal transmission to another cell. If these receptor channels are selective for cations, their opening and the passage of ions causes a change in the membrane potential to more positive values, thus activating signal transmission. Glutamate, serotonin and acetylcholine receptors are excitatory. Opening of anion-permeable receptor-channels causes a change in the membrane potential to more negative values and inhibits signal transmission. The glycine and γ-amino butyric acid ($GABA_A$) are inhibitory. The glycine receptor is activated by glycine, β-alanine, and taurine. It is involved in malfunctions of the nervous system, such as murine spastic disease (Becker et al., "Isoform-Selective Deficit of Glycine Receptors in the Mouse Mutant Spastic," *Neuron* 8:283-289 (1992), which is hereby incorporated by reference in its entirety) and human hyperekplexia (Shiang et al., "Mutations in the α1 Subunit of the Inhibitory Glycine Receptor Cause the Dominant Neurologic Disorder, Hyperekplexia," *Nat. Genet.* 5:351-358 (1993); Rajendra et al., "Startle Disease Mutations Reduce the Agonist Sensitivity of the Human Inhibitory Glycine Receptor," *J. Biol. Chem.* 269:18739-18742 (1994), which are hereby incorporated by reference in their entirety). It is a potential target for general anesthetics and alcohol (Jones et al., "Effects of Volatile Anesthetics on the Kinetics of Inhibitory Postsynaptic Currents in Cultured Rat Hippocampal Neurons," *J Neurophysiol.* 70:1339-1349 (1993); Mascia et al., "Enhancement of Homomeric Glycine Receptor Function By Long-Chain Alcohols and Anesthetics," *Br J Pharmacol* 119: 1331-1336 (1996), which are hereby incorporated by reference in their entirety). Pharmacological intervention at the glycine receptor may provide a means of controlling some kinds of seizure, and a better understanding of the glycine receptor may lead to new anticonvulsant drugs.

Many neurotransmitter receptors and their isoforms of unknown chemical mechanism (Kandel, *Principles of Neuronal Sciences,* 4th ed., New York: McGraw-Hill Inc., (2000), which is hereby incorporated by reference in its entirety) exist. Dysfunctions of neurotransmitter receptor-mediated reactions are implicated in many diseases of the nervous system (e.g. Huntington's disease, Parkinson's disease, epilepsy). Many clinically important compounds (e.g. tranquilizers, antidepressants) and abused drugs (e.g. cocaine) affect receptor function (Hardman, *Goodman and Gilman's The Pharmacological Basis of Therapeutics,* 9th Ed., New York: McGraw-Hill Inc., (1996), which is hereby incorporated by reference in its entirety). In the case of the inhibition of the nicotinic acetylcholine receptor by cocaine, the laser-pulse photolysis technique (Hess et al., "Development and Application of Caged Ligands for Neurotransmitter Receptors in Transient Kinetic and Neuronal Circuit Mapping Studies," *Methods Enzymol: Caged Compd* 291:443-473 (1998), which is hereby incorporated by reference in its entirety) using a caged receptor-activating ligand led to a new mechanism (Hess et al., "Mechanism-Based Discovery of Ligands That Counteract Inhibition of the Nicotinic Cetylcholine Receptor by Cocaine and MK-801," *Proc Natl Acad Sci USA* 97:13895-13900 (2000), which is hereby incorporated by reference in its entirety) and consequently to the first known compounds that prevent inhibition of this receptor by cocaine (Hess et al., "Mechanism-Based Discovery of Ligands That Counteract Inhibition of the Nicotinic Cetylcholine Receptor by Cocaine and MK-801," *Proc Natl Acad Sci USA* 97:13895-13900 (2000); Hess et al., "Reversing the Action of Noncompetitive Inhibitors (MK-801 and Cocaine) on a Protein (Nicotinic Acetylcholine Receptor)-Mediated Reaction," *Biochemistry* 42:6106-6114 (2003), which are hereby incorporated by reference in their entirety). More recently, the laser-pulse photolysis technique using α-CNB-caged γ-aminobutyric (Wieboldt et al., "Synthesis and Photochemistry of Photolabile Derivatives of Gamma-Aminobutyric Acid for Chemical Kinetic Investigations of the Gamma-Aminobutyric Acid Receptor in the Millisecond Time Region," *Biochemistry* 33:1526-1533 (1994), which is hereby incorporated by reference in its entirety) acid was used to elucidate the mechanism of dysfunction of a γ-aminobutyric acid receptor (Ramakrishnan et al., "On the Mechanism of a Mutated and Abnormally Functioning γ-Aminobutyric Acid (A) Receptor Linked to Epilepsy," *Biochemistry* 43:7534-7540 (2004), which is hereby incorporated by reference in its entirety) linked to one form of epilepsy (Baulac et al., "First Genetic Evidence of GABAA Receptor Dysfunction in Epilepsy: a Mutation in the γ 2-Subunit Gene, *Nat Genet* 28:46-48 (2001), which is hereby incorporated by reference in its entirety). On the basis of the mechanism of the mutated receptor (Rarnakrishnan et al., "On the Mechanism of a Mutated and Abnormally Functioning γ-Aminobutyric Acid (A) Receptor Linked to Epilepsy," *Biochemistry* 43:7534-7540 (2004), which is hereby incorporated by reference in its entirety), compounds are being developed to alleviate the dysfunction of the receptor (Cui et al., "Selection of Stable RNA Molecules That Can Regulate the Channel-Opening Equilibrium of the Membrane-Bound γ-Aminobutyric Acid Receptor," *Biochemistry* 43:16442-16449 (2004), which is hereby incorporated by reference in its entirety).

The results obtained in investigations of only very few of the problems related to neurotransmitter receptor mechanisms, employing transient kinetic techniques using caged compounds that require ultraviolet light for photolysis and the use of expensive lasers, appear promising (Hess G., "Rapid Chemical Reaction Techniques Developed for Use in Investigations of Membrane-Bound Proteins (Neurotransmitter Receptors)," *Biophys Chem* 100:493-506 (2003), which is hereby incorporated by reference in its entirety). Caged compounds that can be photolyzed in the visible wavelength region are expected to greatly facilitate these investigations.

Although the invention has been described in detail, for the purpose of illustration, it is understood that such detail is for that purpose and variations can be made therein by those skilled in the art without departing from the spirit and scope of the invention which is defined by the following claims.

What is claimed:

1. A photolabile compound comprising:
    a coumarin family caging group covalently bound to an organic moiety containing a carboxyl group, an amino group, a sulfhydryl group, and/or a hydroxyl group, wherein:
    the organic moiety is an amino acid selected from the group consisting of: aspartic acid; beta alanine; saclofen; S-sulpho-L-cysteine; γ-N-oxalyl-L-α,γ-diaminobutyric acid; O-phospho-D-serine philanthotoxin 343; (±)-cis-2,3-piperidinedicarboxylic acid; piperidine-4-sulphonic acid; L-trans-pyrrolidine-2,4-dicarboxylic acid; isoguvacine; indole-2-carboxylic acid; (+)-α-methyl-4-carboxyphenylglycine; 6-nitroquinoxaline-2,3-dione; γ-D-glutamylaminoethylphosphonic acid; D-homocysteic acid; L-homocysteinesulphinic acid; (RS)-3-hydroxyphenylglycine; 3-hydroxy-2-quinoxaline-carboxylic acid; 5-7-dichlorokynurenic acid; dihydrokainic acid; domoic acid; L-glutamic acid; (S)-4-carboxyphenylglycine; 6-chlorokynurenic acid; D-cysteic acid; L-cysteine sulphinic acid; (±)-3-carboxyphenylalanine; (R)-5-bromowillardiine; aminomalonic acid; and glycine;
    the coumarin family caging group is 7-N,N-diethylamino-4-hydroxymethyl coumarin and is covalently bound to the organic moiety through a hydroxyl group on the coumarin compound and through the carboxyl group, amino group, sulfhydryl group, or hydroxyl group on the organic moiety; and
    the photolabile compound, upon absorbing visible light, releases the organic moiety.

2. The photolabile compound according to claim 1, wherein said organic moiety is caged through the carboxyl group as an ester.

3. The photolabile compound according to claim 1, wherein said organic moiety is caged through the amino group as a carbamate.

4. The photolabile compound according to claim 1, wherein said organic moiety is caged through the sulfhydryl group as a thio ether.

5. The photolabile compound according to claim 1, wherein said organic moiety is caged through the hydroxyl group as an ether or a carbonate of the hydroxyl group.

6. The photolabile compound according to claim 1, wherein said amino acid is a neurotransmitter.

7. The photolabile compound according to claim 1 having the formula:

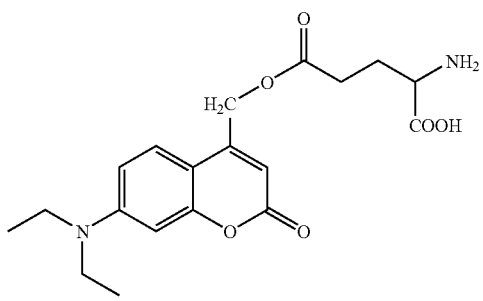

or a trifluoroacetate salt or a biologically compatible salt thereof.

8. The photolabile compound according to claim 1 having the formula:

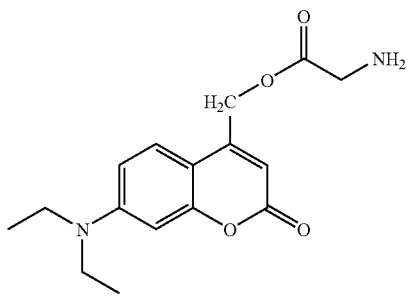

or a trifluoroacetate salt or a biologically compatible salt thereof.

9. The photolabile compound according to claim 1 having the formula:

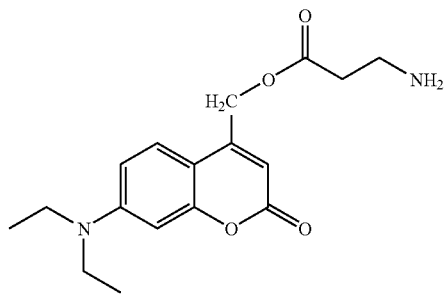

or a trifluoroacetate salt or a biologically compatible salt thereof.

10. The photolabile compound according to claim 1 having the formula:

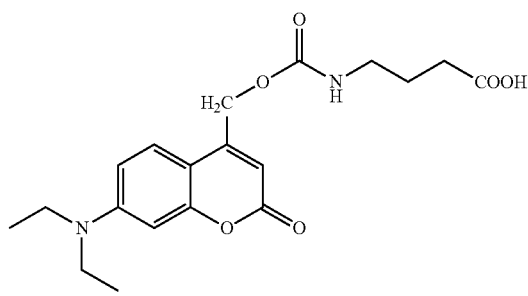

or a trifluoroacetate salt or a biologically compatible salt thereof.

11. The photolabile compound according to claim 1, wherein the compound is water-soluble.

12. The photolabile compound according to claim 1, wherein the compound is biologically inert.

13. The method according to claim 1, wherein the organic moiety is a neurotransmitter and is used for kinetically investigating neurotransmitter-receptor interactions on a surface of a cell in a microsecond to millisecond time domain.

14. The method according to claim 1, wherein the organic moiety is a neurotransmitter and is used for spatially locating neurotransmitter receptors on a cell.

* * * * *

UNITED STATES PATENT AND TRADEMARK OFFICE
CERTIFICATE OF CORRECTION

PATENT NO.       : 8,053,585 B2
APPLICATION NO.  : 11/402715
DATED            : November 8, 2011
INVENTOR(S)      : Hess et al.

It is certified that error appears in the above-identified patent and that said Letters Patent is hereby corrected as shown below:

Column 38, line 38, delete "The method" and insert in its place --The photolabile compound--.

Column 38, line 42, delete "The method" and insert in its place --The photolabile compound--.

Signed and Sealed this
Sixth Day of March, 2012

David J. Kappos
*Director of the United States Patent and Trademark Office*